United States Patent
Flanagan et al.

(10) Patent No.: US 11,793,519 B2
(45) Date of Patent: *Oct. 24, 2023

(54) METHODS AND SYSTEMS FOR DETECTING STAPLE CARTRIDGE MISFIRE OR FAILURE

(71) Applicant: INTUITIVE SURGICAL OPERATIONS, INC., Sunnyvale, CA (US)

(72) Inventors: Patrick Flanagan, Santa Clara, CA (US); David W. Weir, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/391,335

(22) Filed: Aug. 2, 2021

(65) Prior Publication Data

US 2021/0353292 A1 Nov. 18, 2021

Related U.S. Application Data

(63) Continuation of application No. 16/275,858, filed on Feb. 14, 2019, now Pat. No. 11,096,687, which is a
(Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/072* (2013.01);
(Continued)

(58) Field of Classification Search
CPC ............. A61B 17/068; A61B 17/072; A61B 17/07207; A61B 17/00234; A61B 17/115;
(Continued)

(56) References Cited

U.S. PATENT DOCUMENTS

| | | |
|---|---|---|
| 5,383,880 A | 1/1995 | Hooven |
| 5,395,033 A | 3/1995 | Byrne et al. |

(Continued)

FOREIGN PATENT DOCUMENTS

| | | |
|---|---|---|
| CN | 101314224 A | 12/2008 |
| EP | 0630612 A1 | 12/1994 |

(Continued)

OTHER PUBLICATIONS

Extended European Search Report for Application No. EP18152115.4, dated Apr. 16, 2018, 7 pages.

(Continued)

*Primary Examiner* — Scott A Smith
(74) *Attorney, Agent, or Firm* — JONES ROBB, PLLC

(57) ABSTRACT

A system comprises a surgical instrument comprising an end effector comprising a first jaw member and a second jaw member, the second jaw member comprising or being configured to receive a plurality of staples; and an actuation mechanism operably coupled to the end effector to actuate the end effector to perform at least one of a clamping procedure or a staple firing procedure. The system further comprises a drive system configured to drive the actuation mechanism, a controller operably coupled to the drive system, and a user interface operably coupled to the controller, which is configured to determine the clamping procedure or the staple firing procedure has failed based on a magnitude of an actuation force applied by the drive system to the actuation mechanism; and cause the user interface to output a failure indication indicative of the failure.

20 Claims, 25 Drawing Sheets

Related U.S. Application Data continuation of application No. 15/194,771, filed on Jun. 28, 2016, now Pat. No. 10,213,202, which is a continuation of application No. 13/472,431, filed on May 15, 2012, now Pat. No. 9,393,017, which is a continuation-in-part of application No. 13/350,512, filed on Jan. 13, 2012, now Pat. No. 9,226,750.

(60) Provisional application No. 61/443,148, filed on Feb. 15, 2011.

(51) Int. Cl.
| | | |
|---|---|---|
| *A61B 34/30* | (2016.01) | |
| *A61B 17/115* | (2006.01) | |
| *A61B 17/00* | (2006.01) | |
| *A61B 90/00* | (2016.01) | |

(52) U.S. Cl.
CPC ............. *A61B 34/30* (2016.02); *A61B 17/115* (2013.01); *A61B 2017/00017* (2013.01); *A61B 2017/00022* (2013.01); *A61B 2017/00115* (2013.01); *A61B 2017/07214* (2013.01); *A61B 2017/07271* (2013.01); *A61B 2090/064* (2016.02); *A61B 2090/0811* (2016.02)

(58) Field of Classification Search
CPC ........... A61B 2017/07214; A61B 2017/00017; A61B 2017/00022; A61B 2017/07271; A61B 2017/00398; A61B 2090/064; A61B 2090/0811; A61B 34/30
USPC ..... 227/19, 175.2, 176.1, 180.1; 606/1, 139, 606/219
See application file for complete search history.

(56) References Cited

U.S. PATENT DOCUMENTS

| | | | |
|---|---|---|---|
| 5,403,312 | A | 4/1995 | Yates et al. |
| 5,529,235 | A | 6/1996 | Boiarski et al. |
| 5,667,517 | A | 9/1997 | Hooven |
| 5,797,537 | A | 8/1998 | Oberlin et al. |
| 5,916,146 | A | 6/1999 | Allotta et al. |
| 6,315,184 | B1 | 11/2001 | Whitman |
| 6,793,652 | B1 | 9/2004 | Whitman et al. |
| 6,817,508 | B1 | 11/2004 | Racenet et al. |
| 6,849,071 | B2 | 2/2005 | Whitman et al. |
| 7,147,138 | B2 | 12/2006 | Shelton, IV et al. |
| 7,422,136 | B1 | 9/2008 | Marczyk |
| 7,644,848 | B2 | 1/2010 | Swayze et al. |
| 7,717,312 | B2 | 5/2010 | Beetel |
| 7,740,159 | B2 | 6/2010 | Frederick et al. |
| 7,743,960 | B2 | 6/2010 | Whitman et al. |
| 7,784,663 | B2 | 8/2010 | Shelton, IV et al. |
| 7,845,537 | B2 | 12/2010 | Shelton, IV et al. |
| 7,918,230 | B2 | 4/2011 | Whitman et al. |
| 8,012,170 | B2 | 9/2011 | Whitman et al. |
| 8,161,977 | B2 | 4/2012 | Shelton, IV et al. |
| 8,167,185 | B2 | 5/2012 | Shelton, IV et al. |
| 8,453,906 | B2 | 6/2013 | Huang et al. |
| 8,584,919 | B2 | 11/2013 | Hueil et al. |
| 8,758,342 | B2 | 6/2014 | Bales et al. |
| 8,808,311 | B2 | 8/2014 | Heinrich et al. |
| 8,820,603 | B2 | 9/2014 | Shelton, IV et al. |
| 8,820,605 | B2 | 9/2014 | Shelton, IV |
| 8,893,946 | B2 | 11/2014 | Boudreaux et al. |
| 9,226,750 | B2 | 1/2016 | Weir et al. |
| 9,393,017 | B2 | 7/2016 | Flanagan et al. |
| 9,408,606 | B2 | 8/2016 | Shelton, IV et al. |
| 9,445,813 | B2 | 9/2016 | Shelton, IV et al. |
| 9,451,958 | B2 | 9/2016 | Shelton, IV et al. |
| 9,480,476 | B2 | 11/2016 | Aldridge et al. |
| 9,498,219 | B2 | 11/2016 | Moore et al. |
| 9,574,644 | B2 | 2/2017 | Parihar et al. |
| 9,585,658 | B2 | 3/2017 | Timm et al. |
| 9,585,663 | B2 | 3/2017 | Shelton, IV et al. |
| 9,629,629 | B2 | 4/2017 | Leimbach et al. |
| 9,690,362 | B2 | 6/2017 | Leimbach et al. |
| 9,724,094 | B2 | 8/2017 | Baber et al. |
| 9,730,695 | B2 | 8/2017 | Leimbach et al. |
| 9,750,499 | B2 | 9/2017 | Leimbach et al. |
| 9,877,718 | B2 | 1/2018 | Weir et al. |
| 10,213,202 | B2 | 2/2019 | Flanagan et al. |
| 10,758,226 | B2 | 9/2020 | Weir et al. |
| 11,096,687 | B2 | 8/2021 | Flanagan et al. |
| 11,529,203 | B2 * | 12/2022 | Kopp ............... A61B 17/07207 |
| 2005/0131390 | A1 | 6/2005 | Heinrich et al. |
| 2005/0192609 | A1 | 9/2005 | Whitman et al. |
| 2007/0005045 | A1 | 1/2007 | Mintz et al. |
| 2008/0245841 | A1 | 10/2008 | Smith et al. |
| 2009/0054908 | A1 | 2/2009 | Zand et al. |
| 2009/0090763 | A1 | 4/2009 | Zemlok et al. |
| 2009/0188094 | A1 | 7/2009 | Cunningham et al. |
| 2009/0234248 | A1 | 9/2009 | Zand et al. |
| 2009/0260903 | A1 | 10/2009 | Park |
| 2009/0260907 | A1 | 10/2009 | Moshchuk et al. |
| 2009/0260915 | A1 | 10/2009 | Arai |
| 2009/0260919 | A1 | 10/2009 | Beale et al. |
| 2010/0198220 | A1 | 8/2010 | Boudreaux et al. |
| 2010/0228250 | A1 | 9/2010 | Brogna |
| 2010/0312146 | A1 | 12/2010 | Holsten |
| 2011/0155781 | A1 | 6/2011 | Swensgard et al. |
| 2019/0175174 | A1 | 6/2019 | Flanagan et al. |
| 2020/0352563 | A1 | 11/2020 | Weir et al. |

FOREIGN PATENT DOCUMENTS

| | | |
|---|---|---|
| EP | 1728475 A2 | 12/2006 |
| EP | 1997439 A2 | 12/2008 |
| EP | 2044890 A1 | 4/2009 |
| EP | 2127604 A1 | 12/2009 |
| EP | 2277458 A1 | 1/2011 |
| JP | 2004514490 A | 5/2004 |
| JP | 2005523105 A | 8/2005 |
| JP | 2007098130 A | 4/2007 |
| JP | 2009090113 A | 4/2009 |
| JP | 2009189821 A | 8/2009 |
| JP | 2010253272 A | 11/2010 |
| KR | 20070079041 A | 8/2007 |
| WO | WO-0243571 A2 | 6/2002 |
| WO | WO-03020139 A2 | 3/2003 |
| WO | WO-2005112808 A1 | 12/2005 |
| WO | WO-2012112251 A1 | 8/2012 |

OTHER PUBLICATIONS

PCT/US12/021342 International Search Report and Written Opinion of the International Searching Authority, dated Mar. 30, 2012, 15 pages.

PCT/US2012/021319 International Search Report and Written Opinion of the International Searching Authority, dated Mar. 30, 2012, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP23152252. 5, dated Feb. 21, 2023, 10 pages.

* cited by examiner

METHODS AND SYSTEMS FOR DETECTING STAPLE CARTRIDGE MISFIRE OR FAILURE

CROSS-REFERENCES TO RELATED APPLICATIONS

This application is a continuation of U.S. patent application Ser. No. 16/275,858, filed Feb. 14, 2019 (now U.S. Pat. No. 11,096,687) 1, which is a continuation of U.S. patent application Ser. No. 15/194,771, filed Jun. 28, 2016 (now U.S. Pat. No. 10,213,202), which is a continuation of U.S. patent application Ser. No. 13/472,431, filed May 15, 2012 (now U.S. Pat. No. 9,393,017), which is a continuation-in-part of U.S. patent application Ser. No. 13/350,512, filed Jan. 13, 2012 (now U.S. Pat. No. 9,226,750), which claims the benefit of U.S. Provisional Patent Application No. 61/443,148, filed Feb. 15, 2011, each of which is incorporated herein by reference in its entirety.

The present application is related to U.S. Provisional Application No. 61/551,880, entitled "Cartridge Status and Presence Detection," filed on Oct. 26, 2011; U.S. Provisional Application No. 61/560,213 entitled "Cartridge Status and Presence Detection," filed on Nov. 15, 2011; U.S. application Ser. No. 12/945,541 entitled "End Effector with Redundant Closing Mechanisms," filed on Nov. 12, 2010; U.S. Provisional Application No. 61/260,907, entitled "END EFFECTOR WITH REDUNDANT CLOSING MECHANISMS," filed on Nov. 13, 2009; U.S. Provisional Application No. 61/260,903, entitled "WRIST ARTICULATION BY LINKED TENSION MEMBERS," filed on Nov. 13, 2009; U.S. Provisional Application No. 61/260,915, entitled "SURGICAL TOOL WITH A TWO DEGREE OF FREEDOM WRIST," filed on Nov. 13, 2009; and U.S. Provisional Application No. 61/260,919, entitled "MOTOR INTERFACE FOR PARALLEL DRIVE SHAFTS WITHIN AN INDEPENDENTLY ROTATING MEMBER," filed on Nov. 13, 2009; each of which is incorporated herein by reference in its entirety.

INTRODUCTION

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure by means of a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing an image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Non-robotic linear clamping, cutting and stapling devices have been employed in many different surgical procedures. For example, such a device can be used to resect a cancerous or anomalous tissue from a gastro-intestinal tract. Unfortunately, many known surgical devices, including known linear clamping, cutting and stapling devices, have opposing jaws that may generate less than a desired clamping force, which may reduce the effectiveness of the surgical device. Devices have been developed generating higher levels of clamping forces for applicable surgical procedures (e.g., tissue stapling), however, clamping with high force jaws periodically fails. Additionally, firing of staples to seal tissue may fail. Detecting failure in clamping or firing of a staple has proven difficult in some minimally invasive surgical applications, however, since a surgeon may not have a clear view of the tissue being clamped or stapled and a tool inserted into a body is constrained by significant size and space limitations. Since a surgeon's tactile feedback in a robotic system can be somewhat limited, a surgeon may not realize when failure has occurred until after the clamping or firing procedure is complete.

In light of the above, it would be desirable to enable a surgeon to detect clamping or staple firing failure at the time it occurs, so that the procedure can be suspended or modified to reduce the likelihood of tissue damage and/or to allow the surgeon to mitigate the effects of any tissue which has been damaged. Given the limitations associated with a minimally invasive surgical environment, it would be desirable to detect failure from outside the body without substantially adding to the profile of the end effector.

Thus, methods and system which can detect failure and indicate failure to the user, yet are compatible with the demands of minimally invasive procedures are desirable. Such tools may be beneficial in surgical applications, particularly in minimally invasive surgical applications.

SUMMARY

Improved systems and methods to detect and indicate clamping and/or staple firing failure are provided. The claimed methods and systems relate to detecting whether clamping of a material grasped between jaws or firing of a staple into the clamped material is likely to fail. The claimed systems and methods may detect failure in clamping or firing during the process of clamping or firing, thereby reducing the potential for tissue damage from continuing to clamp or fire a staple after failure has occurred. The claimed systems and methods are particularly useful in surgical applications involving clamping of a body tissue between two jaws of an end effector and firing of a staple into the clamped tissue. Many surgical applications require clamping of a body tissue at a clamping force sufficient for cutting, sealing and/or stapling of the clamped tissue. Since clamping and firing of a staple may require relatively higher forces than tissue manipulation, failure in clamping or firing may potentially cause damage to the delicate tissues. The present methods and systems are particularly advantageous in minimally invasive surgical applications as they indicate failure as soon as it occurs and allows for detection of failure from outside the body. While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

In a first aspect, the teachings provide a method of detecting failure in clamping of a material between jaws driven by an actuator, such as a motor or detecting failure in firing of staple, the firing force being driven by an actuator, such as a motor. The method includes monitoring a drive parameter of the actuator or motor during application of a clamping or firing force and, in response to the monitored drive parameter, outputting an indication on a user interface of clamping or firing failure. Typically, an indication of clamping or firing failure occurs when the monitored drive parameter of the actuator, such as a torque output of a motor or displacement of a driving mechanism, is outside an acceptable range of drive parameters. The indication may also be indicative of a likelihood of clamping or firing failure, wherein the likelihood of failure falls within a gradient between a first and second likelihood, the first likelihood being likely failure and the second likelihood being likely success. In many embodiments, the material clamped and stapled is a body tissue, including an outer skin or internal organs, such as a bowel, stomach or lung.

In accordance with the present teachings, various exemplary methods and systems disclosed herein include monitoring a drive parameter during clamping between a first and second jaw of an end effector or during firing of a staple into clamped tissue. Often, the clamped tissue is cut after opposing sides of the tissue along the cutting line are stapled by one or more rows of surgical staples to seal the tissue. The end effector is generally part of a minimally invasive robotic surgical system. The clamp may include first and second jaws that may comprise two separate jaws or a first jaw articulable against a portion of the end effector, in which case the portion of the end effector comprises the second jaw. In one aspect, the methods include clamping of a material between the first and second jaw of an end effector or firing of a staple into the clamped material, typically in response to a command from a user to clamp or fire. The system effects clamping or firing by applying a force to a clamping mechanism and/or a force to form a staple. As the clamping or firing occurs, the system monitors the drive parameter of the actuator applying the force to clamp or fire. In response to the monitored drive parameter, the system outputs an indication on a user interface of clamping or firing progress, failure or success.

In many exemplary embodiments in accordance with present teachings, an indication of likely clamping or firing failure is provided in response to the monitored drive parameter being outside an acceptable range of desired drive parameters of the actuator, such as a range of torque outputs. Often, the acceptable range of drive parameters vary with the displacement and/or the position and/or the velocity of the actuator or motor, such that the acceptable range of drive parameters may be different depending on the configuration of the end effector. For example, the acceptable range of drive parameters at an initial displacement of the actuator or motor (as the clamp starts from an open configuration) may be different from the acceptable range of drive parameters at a final displacement (such as when the jaw is in a closed/clamped configuration). The same is true for the different initial configuration and final configuration of the firing mechanism. The system may detect the configuration of the end effector by sensing the displacement or position of the actuator effecting movement, or the mechanism through which the actuator effects clamping or firing. Configuration of the end effector also may be detected by communication between a replaceable staple cartridge and a robotic interface. Examples of such configuration detection are discussed in U.S. Provisional Application No. 61/551,880, entitled "Cartridge Status and Presence Detection," filed on Oct. 26, 2011, and U.S. Provisional Application No. 61/560,213 entitled "Cartridge Status and Presence Detection," filed on Nov. 15, 2011, the entire contents of each of which is incorporated herein by reference. The clamping or firing is effected by the drive parameter through one or more mechanisms coupling the actuator to the end effector and/or the staple. The mechanism(s) may include a cable, a hypotube, a gear, or a lead screw. In many embodiments, the indication of likely clamping failure is a visual indicator shown on a display of a user interface, but also may be communicated to the user by an audio signal, visual signal, or other sensory indicator.

In accordance with another aspect of the present teachings, exemplary methods of controlling a surgical stapler system are disclosed. Such exemplary methods include monitoring an initial actuation force applied to a stapler cartridge of the surgical stapler system and comparing the initial actuation force to a threshold actuation force. Continued application of actuation force to the cartridge is based on the comparison. A threshold force greater than the initial actuation force provides an indication of cartridge misfire or failure, and a staple firing sequence may be terminated in response to such a determination. The initial actuation force and the threshold force may be linear forces, or rotary forces (torques), applied to the cartridge by a drive system of the surgical stapler system. In response to a determination that a cartridge misfire or failure is occurring, the system outputs an indication on a user interface of cartridge misfire or failure and the firing sequence is terminated. Subsequent to the comparison of the initial actuation force to the threshold actuation force, the continuing actuation force applied during the remainder of the stapling sequence. Such monitoring compares the continuing actuation force to a minimum threshold and a maximum threshold. A continuing actuation force below the minimum threshold or above the maximum threshold provides an indication of cartridge misfire or failure, and the staple firing sequence may be terminated in response to such a determination.

According to one aspect of the disclosure, a surgical stapler system in accordance with the present teachings includes an end effector having a portion that removably receives a staple cartridge, a drive system that applies an initial actuation force to the staple cartridge, and a sensor for measuring the initial actuation force applied to the staple cartridge. A controller is communicatively coupled to the sensor and the drive system to receive a signal indicative of the initial actuation force applied to the staple cartridge and to control a staple firing sequence based on a comparison of the initial actuation force and a threshold actuation force. In response to a determination that a cartridge misfire or failure is occurring, the system outputs an indication on a user interface of cartridge misfire or failure. In response to a determination that a cartridge misfire or failure is occurring, the system terminates a staple firing sequence. Subsequent to the initiation of the firing sequence, the controller continues to receive a signal indicative of the actuation force as the firing sequence progresses (the measured actuation force). The controller compares the measured actuation force to a minimum threshold force and a maximum threshold force. If the controller determines that the measured actuation force falls below the minimum threshold force or exceeds the maximum threshold force, the controller may terminate the staple firing sequence.

In accordance with another aspect of the present teachings, an exemplary method or system may suspend driving of the actuator in response to an indication of failure or likely failure in clamping or firing of the staple. The methods may also include maintaining a driving parameter after an indication of failure, or maintaining a driving parameter driving clamping while suspending a force driving firing of a staple. In many embodiments, the clamping mechanism is non-back driveable such that no input is needed to maintain the clamping force once it is applied or established. In such cases, an input may be needed to unclamp and reverse the motion of the lead screw. The methods may include reversing a driving force so as to unclamp after outputting the indication of failure.

In accordance with the present teachings, exemplary embodiments of a system include an end effector, a sensor, and a user interface. A first and second jaw of the end effector are coupled to an actuator such that driving the actuator produces a clamping force so as to clamp a material between the first and second jaws. The system may also include an actuator, such as a motor, releasably coupled to a stapling cartridge such that driving the actuator produces a firing force so as to fire the staple through the clamped material and forming it into a closed shape. The clamping and firing actuator may be a single actuator or may be separate actuators. The system may include a sensor for monitoring the drive parameters applying the clamping or firing forces to the end effector. The sensor may be a separate sensor or may be incorporated into the robotic surgical system and may also monitor a displacement of the motor or mechanism. The systems may also include a processor for comparing the monitored drive parameter with a desired drive parameter or range of parameters. The processor may also determine the range of acceptable drive parameters for a given displacement.

The system may comprise a first and second actuation mechanism for effecting clamping and firing, respectively. The first and second actuation mechanisms can employ different force transmission mechanisms corresponding with the force requirements for the clamping mode and the firing force mode. For example, a force used by the first jaw actuation mechanism to move the jaw from the open to the close position can include a linear force or a torque (rotational force), and a force used by the second jaw actuation mechanism to fire a staple through the tissue can include a linear force or a torque. In many embodiments, the first actuation mechanism includes a lead screw-driven mechanism for use in the high force clamping mode, and the second actuation mechanism includes a second lead screw-driven mechanism for use in the firing of the staple. Alternatively, the clamping and firing may utilize a portion of or the same mechanism.

For a fuller understanding of the nature and advantages of the present teachings, reference should be made to the ensuing detailed description and accompanying drawings. Other aspects, objects and advantages of the present teachings will be apparent from the drawings and detailed description that follows.

DETAILED DESCRIPTION

Figure 1:
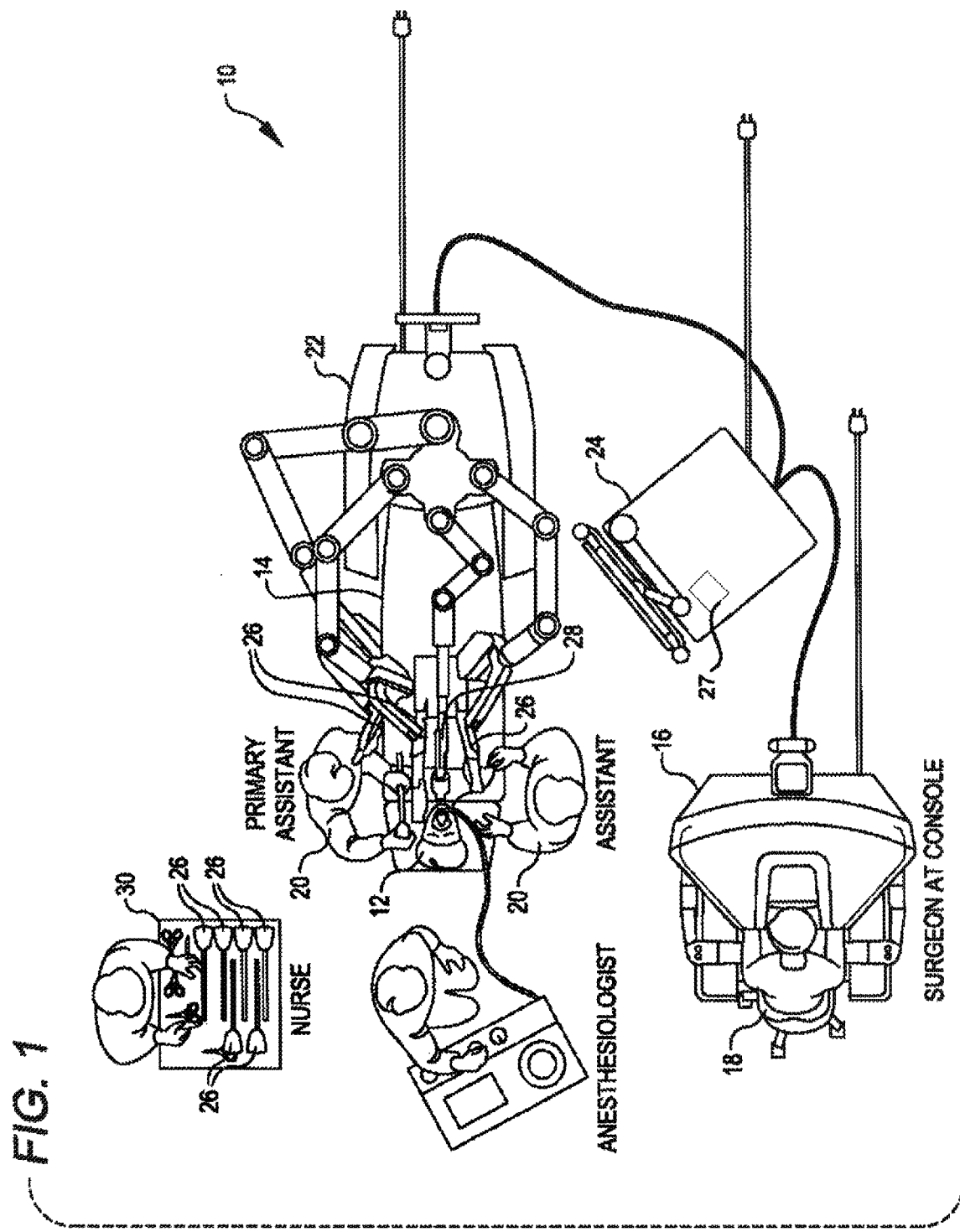
FIG. 1 is a plan view of a minimally invasive robotic surgery system being used to perform a surgery, in accordance with many embodiments.

Improved systems and methods related to clamping and/or fastener firing are provided. The present teachings relate to providing an indicator of whether clamping of a given material fails during clamping. The teachings may be used in systems having jaw members for clamping a material or firing of a staple into a clamped material. The claimed system and methods are particularly useful for minimally invasive surgical applications, as they allow for failure detection in constrained environments from outside the body. Such systems often include end effectors having jaws that clamp a body tissue and fire a staple into the tissue at a relatively high force. Clamping at a high clamping force allows the user to perform various procedures requiring a hard clamp. For example, a physician may require a hard clamp of body tissues before cutting, sealing or stapling of tissue. Firing of staples or other fasteners may also require use of relatively high forces to drive the staple through the body tissue and form the staple. Since clamping and staple firing utilize relatively high forces applied in a confined surgical area, clamping or firing failure has the potential to damage delicate tissues. Additionally, stapling cartridges used in surgical stapling procedures may include a knife for cutting tissue between stapled areas. If the stapling system fails or misfires, such that staples are not deployed but the knife is deployed to cut the target tissue, tissue damage may occur.

Methods and systems in accordance with the present teachings are advantageous as they allow detection of clamping or firing failure during the clamping or firing process from outside the body without increasing the profile of the end effector. Such methods and systems allow for increased capabilities and safety for the patient while maintaining the reduced scale of the minimally invasive surgical tools. While the various embodiments disclosed herein are primarily described with regard to surgical applications, these surgical applications are merely example applications, and the disclosed systems and methods can be used in other suitable applications, both inside and outside a human body, as well as in non-surgical applications.

Typically, a system utilizing the present teachings includes an end effector having two jaws for clamping a material and/or firing a staple or fastener through the clamped material. The two jaws may comprise an articulated jaw attached to an end effector, such that moving the articulated jaw towards a portion of the end effector, the second jaw being that portion of the end effector. In many embodiments, the system uses two independent mechanisms to articulate the jaws of the end effector. A first actuation mechanism provides a fast response/low force mode that varies the position of the articulated jaw between a closed (grasped) configuration and an open configuration. In many embodiments, the first actuation mechanism is back-drivable. For example, in the low force grasping mode, the first actuation mechanism can be designed to provide, for example, 5 pounds of clamping force between the tips of the first and second jaw. A second actuation mechanism provides a high force clamping mode for clamping the body tissue between the jaws at the higher clamping force. Often, the second actuation mechanism is non-back-drivable. The second actuation mechanism often converts a relatively weak force or torque (but with large displacement available) to a relatively high force, closing the jaw of the end effector. The second actuation mechanism can be designed to provide, for example, 50 pounds of clamping force between the tips of the clamped jaws.

Typically, in applications using various exemplary methods in accordance with the present disclosure, a surgeon clamps the body tissue at the relatively high clamping force and once clamped, fires a series of staples through the clamped tissue thereby sealing the tissue. If the jaws should fail to clamp completely, the resulting stapling and cutting may not provide adequate mechanical sealing of the tissue. Clamping force is related to the characteristics of the material, such as tissue, being clamped. Also relevant is the starting thickness of the material being clamped, its compressibility, and the size or area of the material being clamped. Clamping of the tissue may fail for a variety of reasons, including too much tissue being grasped or insufficient tissue grasped between the jaws, including interference from an adjacent tissue, such as a bone, or slippage of the tissue from between the jaws. Even if clamping is successful, firing of a staple or other fastener may fail for a variety of reasons, including, for example, inadvertent reuse of a previously fired cartridge, missing staples, a jammed staple, inconsistencies in the material, interference from another material, or slippage of the clamped material. The staple firing force may be determined by the staple geometry and material from which the staple is formed. Wire diameter, staple leg length, and sharpness of the staple tip may factor into firing force. The highest force is seen just prior to the initial bending of the staple leg after it has penetrated the compressed material (tissue). This is referred to as the buckling load.

Therefore, it would be advantageous for systems and methods that can detect when clamping or firing failure occurs during the process of clamping or firing and indicate such failure to a physician, thereby reducing the likelihood that tissue damage will result. Ways in which tissue damage can be avoided by use of the claimed methods, include: terminating the clamping or firing process or allowing the user to terminate or modify the process after failure has been indicated or advance warning of a firing failure before the material in the jaws is unclamped and released. The described systems and methods detect such failures and provide an indication to the user of failure or likely failure during clamping and/or staple firing into a clamped material. Clamping may be considered successful when in the clamped position, the distance between the jaws are sufficient for performing a therapy, such as firing a staple through the clamped tissue. This distance may vary according to various factors, including the type of tissue, type of treatment, or the dimensions of a staple to be fired through the clamped tissue. In one aspect, the claimed methods and systems detect failure by monitoring one or more drive parameters of an actuator or motor that drives the clamping and/or staple firing. In at least one embodiment, the motor provides a drive parameter or force output, such as a torque, to a mechanism so as to effect clamping and/or firing of a staple with the end effector. The system may determine whether the drive parameter is within an acceptable range of desired drive parameters. The acceptable range of drive parameters may vary according to the displacement, position, or velocity of the motor or the mechanism effecting movement. Typically, if clamping or firing fails, the force output of the driving motor drops below a minimum acceptable or lower threshold force, such as from an absence of material between clamping jaws, or the force output may spike above a maximum acceptable or upper threshold force, such as from clamping on a bone or jamming of the mechanism. Continuing driving of the motor in either case may result in damage to surrounding materials or tissue or to the motor or system itself. By monitoring the force output of the driving motor during clamping of the material and/or firing into the tissue, the claimed methods and systems detect failure or likely failure during clamping or firing and output an indication of such failure or likely failure to the user. Additionally, the system and methods may automatically terminate the clamping or firing or wait for further input from the user after providing an indication of failure. Ideally, the methods include monitoring a drive parameter.

Minimally Invasive Robotic Surgery

Referring now to the drawings, in which like reference numerals represent like parts throughout the several views, FIG. 1 is a plan view illustration of an embodiment of the present teachings. FIG. 1 illustrates a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot), and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. Tool assembly 26 includes end effector 25, the end effector having jaws for clamping the tissue and a mechanism for firing a staple through the clamped tissue. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. Electronics Cart 24 includes a Processor 27 for monitoring the drive parameter provided by the motor output to the end effector. Processor 27 may monitor the drive parameter by comparing the drive parameter to an acceptable range of drive parameters. As the acceptable range of drive parameters may vary with the displacement, position, or velocity of the actuator or the mechanism effecting movement of the end effector, the Processor 27 may also receive displacement data as to the displacement of the actuator or the end effector mechanism during clamping and/or firing such that Processor 27 compares the monitored drive parameters against a range of acceptable drive parameters for any given displacement, position, or velocity. The displacement data may be measured directly or may be determined from positional data, or derivatives thereof, obtained by the robotic system, such as a robotic patient-side manipulator (PSM) system, for example, described in U.S. Patent Application Publication No. 2007/0005045, the entire contents of which are incorporated herein by reference. In response to the monitored drive parameter, Processor 27 may output a clamping failure indication to a user interface. The system 10 then communicates an indicator of the prediction to the physician on the Surgeon's Console 16 so as to communicate to the surgeon whether clamping or firing has failed.

Figure 2:
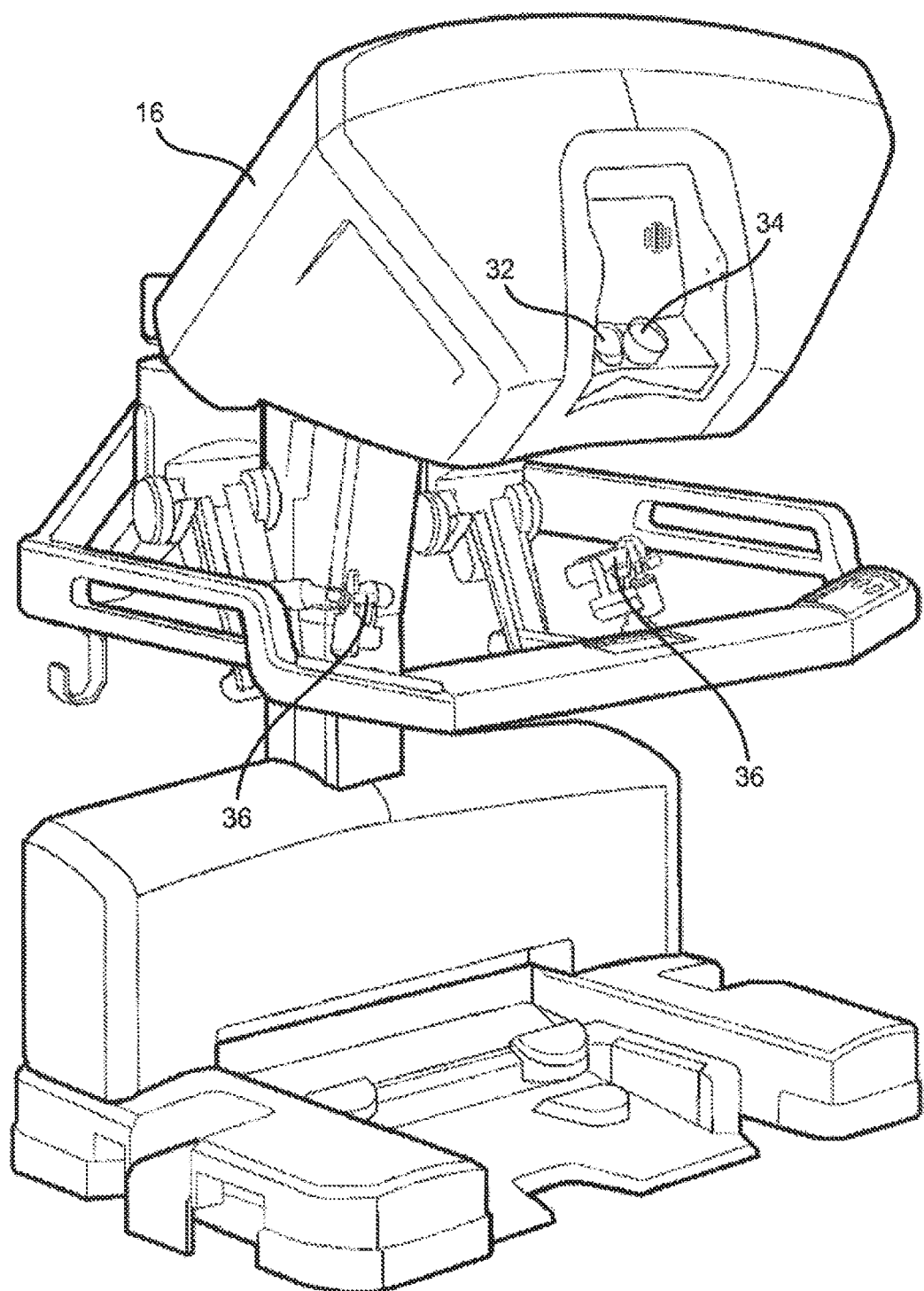
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
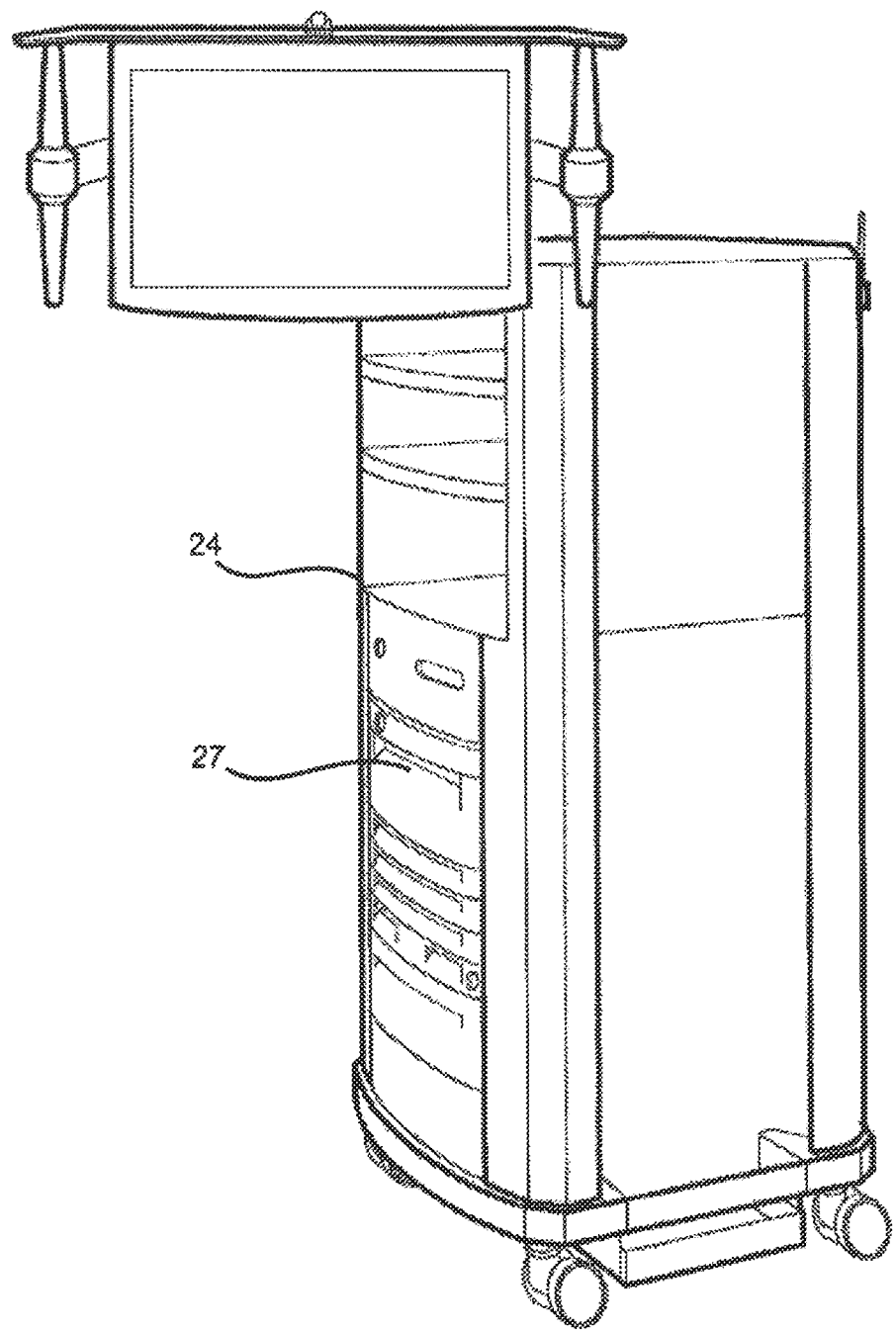
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include Processor 27 to monitor the drive parameter and to determine an indication of clamping failure in response to the monitored drive parameter. Processor 27 may also process captured images for subsequent display, such as to a Surgeon on the Surgeon's Console, or on any other suitable display located locally and/or remotely.

Figure 4:
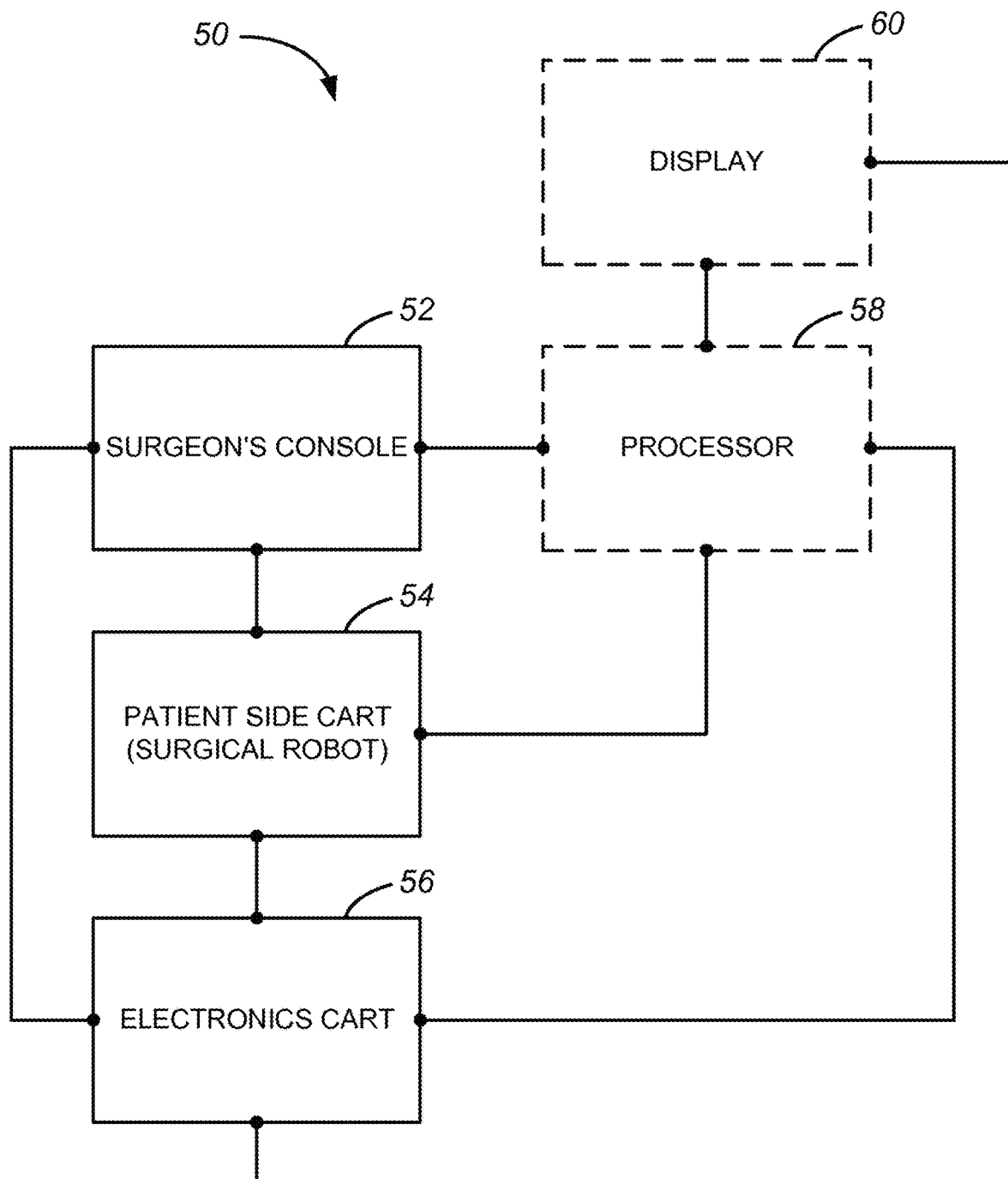
FIG. 4 diagrammatically illustrates a robotic surgery system, in accordance with many embodiments.

FIG. 4 diagrammatically illustrates a robotic surgery system 50 (such as MIRS system 10 of FIG. 1), in which the Processor 58 and Display 60 are depicted separately from Electronics Cart 56 and Surgeon's Console 52. As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. In preparation for firing a staple to seal a body tissue, the Surgeon can command the tool of the Patient Side Cart 54 to clamp between jaw members of an end effector. In response to this command, Processor 58 can command the system to begin driving the motor to engage a mechanism that begins moving the jaws together and increase a clamping force to a desired clamping force. As the jaws begin moving together and the clamping force increases, the Processor 58 continuously monitors one or more drive parameters of the motor and compares the drive parameters to an acceptable range of drive parameters as the motor drives the jaws to clamp at a desired clamping force. If at any point during clamping, the drive parameter exceeds or drops below an acceptable drive parameter, Processor 58 may output the indication of clamping failure on the user interface. In response to detection of clamping failure, Processor 58 may also command additional functions, such as suspending driving of the motor, preventing firing of the staple, maintaining the clamping force at the point of detected clamping failure, waiting for user input, and unclamping the tissue. Similarly, the Processor 58 continuously monitors the drive parameter during firing of a staple through successfully clamped tissue. In response to the drive parameter falling outside the acceptable range of desired drive parameters, Processor 58 may output a failure indication on the user interface. In response to detected firing failure, Processor 58 may command one or more other functions, such as terminating firing or a firing sequence, terminating deployment of the knife blade to cut target tissue, suspending driving of the motor, maintaining clamping of the tissue while preventing firing, or waiting for user input. Processor 58 may monitor the drive parameter during a single action, such as the firing of a single staple, or may continue to monitor the drive parameter throughout a surgical process such as a firing sequence in which a plurality of staples are deployed and tissue between stapled areas is cut.

One of skill in the art would appreciate that an indication of clamping failure may include an indication of how likely clamping failure may be. For example, the Processor 58 may output an indication of clamping failure indicating the likelihood of clamping failure from a 0% chance of failure to a 100% chance of failure, thus allowing the user to adjust or terminate the procedure before actual failure occurs based on an increase in the likelihood of failure as indicated by the failure indication. In some embodiments, if the monitored drive parameter is within the acceptable range of drive parameters, then a failure indicator that express a likelihood of failure may express a likelihood of failure that falls within a range of 0 to 49%. In another embodiment, this range may be expressed as a gradient, including a non-numerical gradient, such as a color gradient. Depending on the likelihood of failure as communicated by the failure indicator, the Surgeon may then safely proceed with clamping of the body tissue or may abort clamping and reposition the jaws until Display 60 indicates a higher likelihood of clamping or firing success.

Figure 5B:
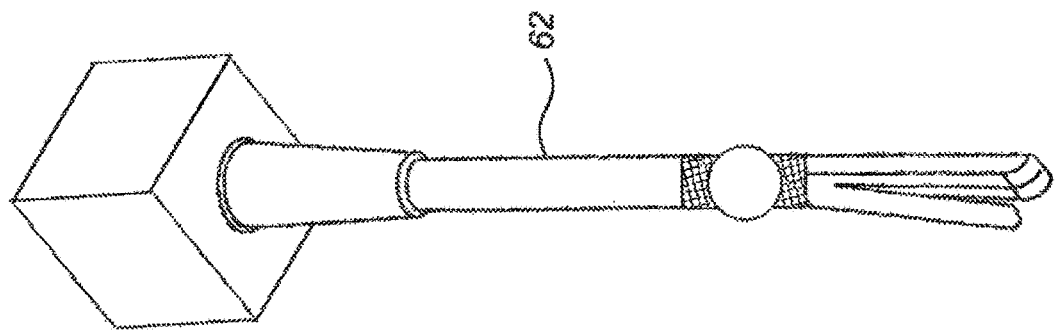
FIG. 5B is a front view of a robotic surgery tool.
Figure 5A:
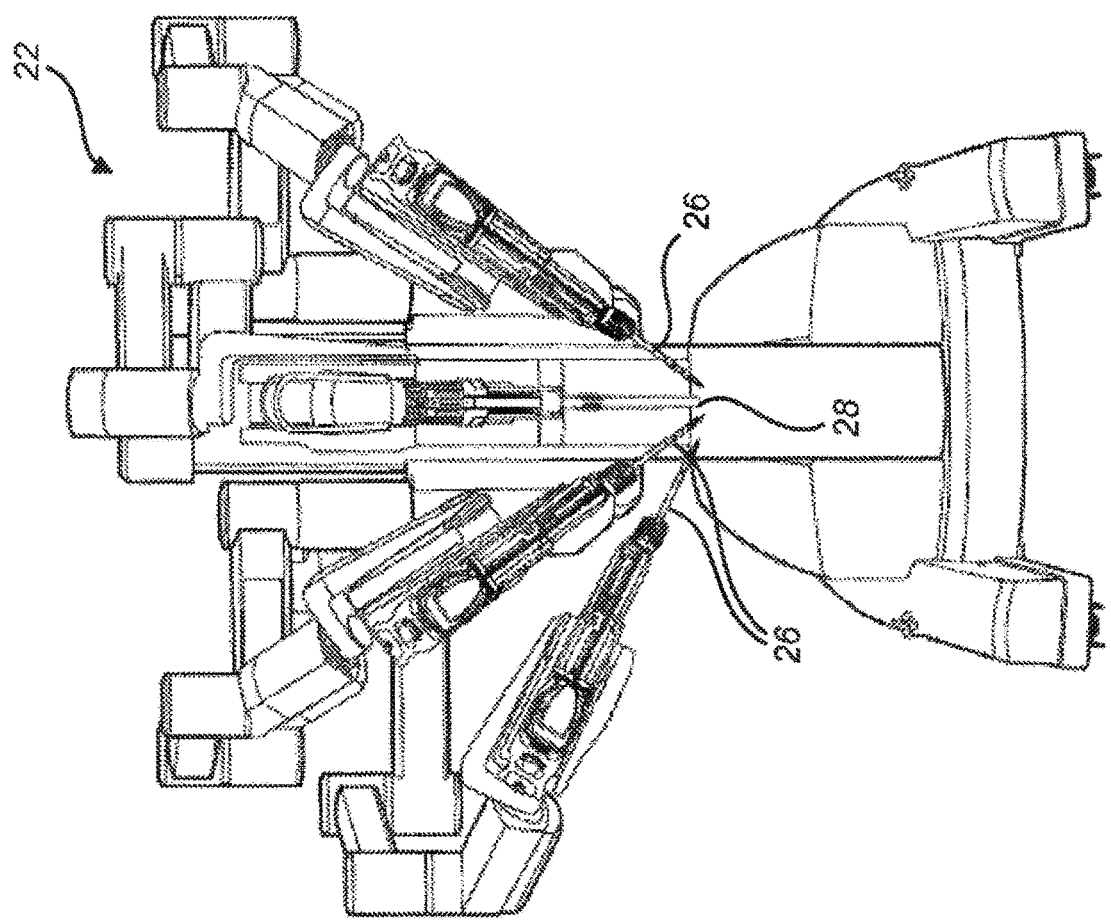
FIG. 5A is a front view of a patient side cart (surgical robot) of a robotic surgery system, in accordance with many embodiments.

FIGS. 5A and 5B show a Patient Side Cart 22 and a surgical tool 62, respectively. The surgical tool 62, one of the surgical tools 26, is an example of an end effector having a set of jaw members for clamping a tissue and firing a staple into the clamped tissue. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Tissue Clamping and Staple Firing with Independent Actuation Mechanisms

In accordance with the present teachings, some exemplary embodiments utilize two independent actuation mechanisms to control the articulation of an articulated jaw of an end effector. A first actuation mechanism can be used to provide a high force clamping mode, and a second actuation mechanism can be used to provide a high force firing mode. In many embodiments, the first and second actuation mechanism used to provide the high clamping force and high firing force is non-back-drivable. The first and second actuation mechanisms may comprise a first and a second lead screw. Using independent actuation mechanisms may be beneficial in some surgical applications, for example, electrocautery sealing, stapling, etc., which may require different forces for different functions during the same procedure.

In various exemplary embodiments disclosed herein, actuation of the jaws in the high clamping force mode is provided by a lead screw actuation mechanism that includes a lead screw driven cam. The driven cam interfaces with a mating cam surface on the articulated jaw so as to hold the articulated jaw in a closed (clamped) configuration when the lead screw driven cam is at a first end of its range of motion. In addition, the driven cam does not constrain motion of the articulated jaw when the lead screw driven cam is at a second end (opposite end) of its range of motion. In other words, the mating cam surfaces are arranged such that motion of the lead screw driven cam in one direction will cause the articulated jaw to close, and motion of the lead screw driven cam in the reverse direction will allow (but not force) the articulated jaw to open to a limit provided by the cam surfaces. Often, the lead screw actuation mechanism is non-back-drivable. In many embodiments, the position of the jaw members of the end effector can be determined by the position of the cable actuation mechanism, or if driven by a lead screw, the position of the lead screw. The system may include a dual drive actuator having a drive for effecting clamping at a clamping force and a drive for effecting firing a staple at a firing force. The actuator may utilize an existing motor or drive, or utilize an additional drive or motor, to effect firing of the staple. The claimed methods and systems monitor the drive parameter of whichever motor, or motors, which are driving the clamping or firing. Additionally, terminating or stopping driving of the motor when failure is detected may also comprise continuing driving of another drive or motor affecting another function. For example, if firing failure is indicated, the system may stop driving the firing force, while still maintaining the driving of the clamping force and wait for a user to unclamp the tissue.

Figure 6A:
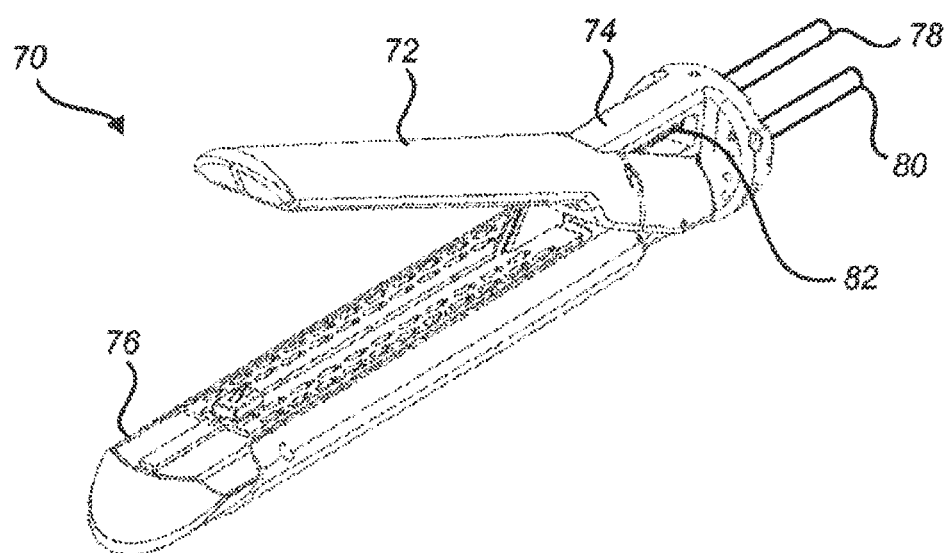
FIG. 6A is a perspective view of an end effector having an articulated jaw, in accordance with many embodiments.

FIG. 6A is a perspective view of an end effector 70 having a jaw 72 articulated by two independent actuation mechanisms, in accordance with many embodiments. The end effector 70 includes an end effector base 74, the articulated jaw 72, and a detachable stationary jaw 76 (an attached removably mountable cartridge), which holds the staples. The end effector 70 is actuated via a first drive shaft 78, a second drive shaft 80, and two actuation cables (not shown). The first drive shaft 78 rotates a lead screw 82 of a lead screw actuation mechanism, the lead screw 82 located within the stationary jaw 76. The second drive shaft 80 rotates another lead screw (not shown) of the detachable stationary jaw 76.

In many embodiments, the first drive shaft 78 and/or the second drive shaft 80 are driven by drive features located in a proximal tool chassis to which the end effector 70 is coupled with via an instrument shaft. In many embodiments, the proximal tool chassis is configured to be releasably mountable to a robotic tool manipulator. In many embodiments, the first drive shaft 78 and the second drive shaft 80 are actuated via respective drive features located in the proximal tool chassis. In many embodiments, such drive features are driven by motors that are located in the proximal tool chassis.

Figure 6B:
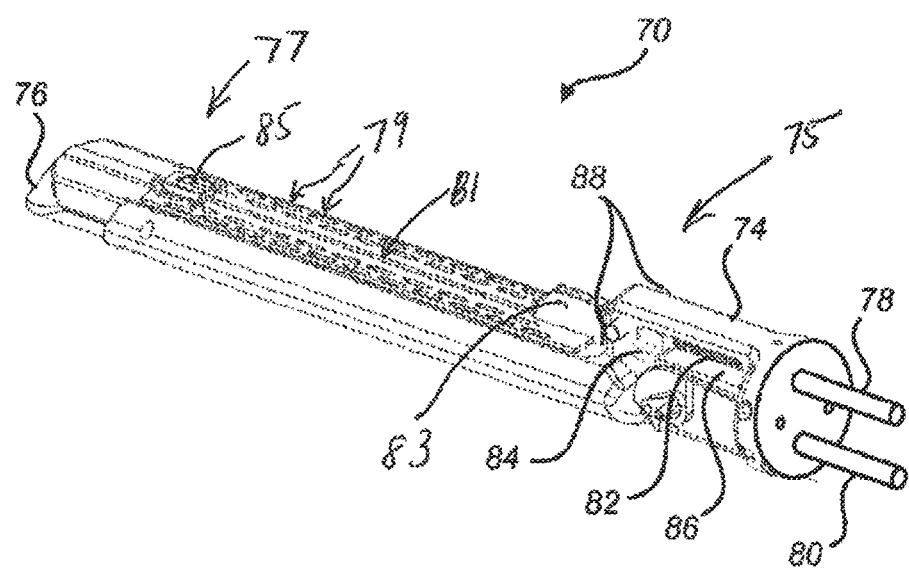
FIG. 6B is a perspective view of the end effector of FIG. 6A (with the articulated jaw removed to better illustrate lead screw actuation mechanism components), in accordance with many embodiments.

FIG. 6B is a perspective view of the end effector 70 of FIG. 6A (with the articulated jaw 72 removed to better illustrate components of the lead screw actuation mechanism and the stationary jaw/staple cartridge 76), in accordance with many embodiments. The lead screw 82 is mounted for rotation relative to the end effector base 74. A lead screw driven cam 84 is coupled with the lead screw 82 so that selective rotation of the lead screw 82 can be used to selectively translate the lead screw driven cam 84 along a cam slot 86 in the end effector base 74. The end effector 70 includes a pivot pin 88 that is used to rotationally couple the articulated jaw 72 with the end effector base 74.

The stationary jaw/staple cartridge 76 acts as a lower jaw of the end effector or is attached to a lower jaw of an end effector. An upper jaw, such as articulated jaw 72, is positioned above an upper surface of staple cartridge 76. Staple cartridge 76 has a proximal end 75 that is attached to the base 74 of the end effector and a distal end 77 disposed at a corresponding distal end of the end effector. The upper surface of cartridge 76 includes four or six rows of staple openings 79, a longitudinal slot 81, a proximal knife garage 83, a distal knife garage 85, and a rotational input (not shown). In many embodiments, a staple is disposed in each of the staple openings for deployment therefrom. A drive member (not shown) positioned within the body of cartridge 76 and mounted on or connected to a lead screw (not shown) is movable in a distal direction within the cartridge 76 to dispense the staples, pushing the staples up through the openings 79, through tissue clamped between the staple cartridge 76 and articulated jaw 72, into articulated jaw 72 such that contact with jaw 72 causes the staples to close or fasten to the tissue.

The longitudinal slot 81 accommodates a cutting blade of a knife member (not shown) extending therefrom as the knife member is moved from the proximal knife garage 83 to the distal knife garage 85. In operation, an actuator of the surgical instrument, such as a surgical stapler or a robotic surgical stapler, is drivingly coupled to a rotary input of the cartridge 76 and applies a rotational force or torque to the rotary input of the cartridge 76, causing actuation of the lead screw and movement of the drive member from a proximal end to a distal end of the cartridge 76. Movement of the drive member initiates deployment of the staples starting at the cartridge proximal end 75 and proceeding to the cartridge distal end 77. The knife blade or cutting blade is deployed after stapler firing actuation begins, moving from the proximal knife garage to the distal knife garage. Movement of the knife blade lags behind and follows the deployment of staples, such that the knife blade remains substantially stationary until the lead screw has caused the drive member to travel a sufficient distance to begin forming and deploying the staples. The lag distance between firing actuation (staple deployment) and knife blade movement causes the cut line to trail the stapling of the tissue to ensure that only fully stapled tissue is cut (i.e., minimizes the risk of cutting unstapled tissue). A sensor for sensing, e.g., measuring, the rotary output of the surgical instrument may be communicatively coupled to a processor and provide a signal indicative of the output of the surgical instrument to the processor for controlling a firing sequence of the surgical stapler instrument.

FIGS. 7A-10 illustrate the actuation mechanisms by which an end effector clamps a body tissue between its jaws clamping mode and fires a staple into the clamped tissue.

Figure 7A:
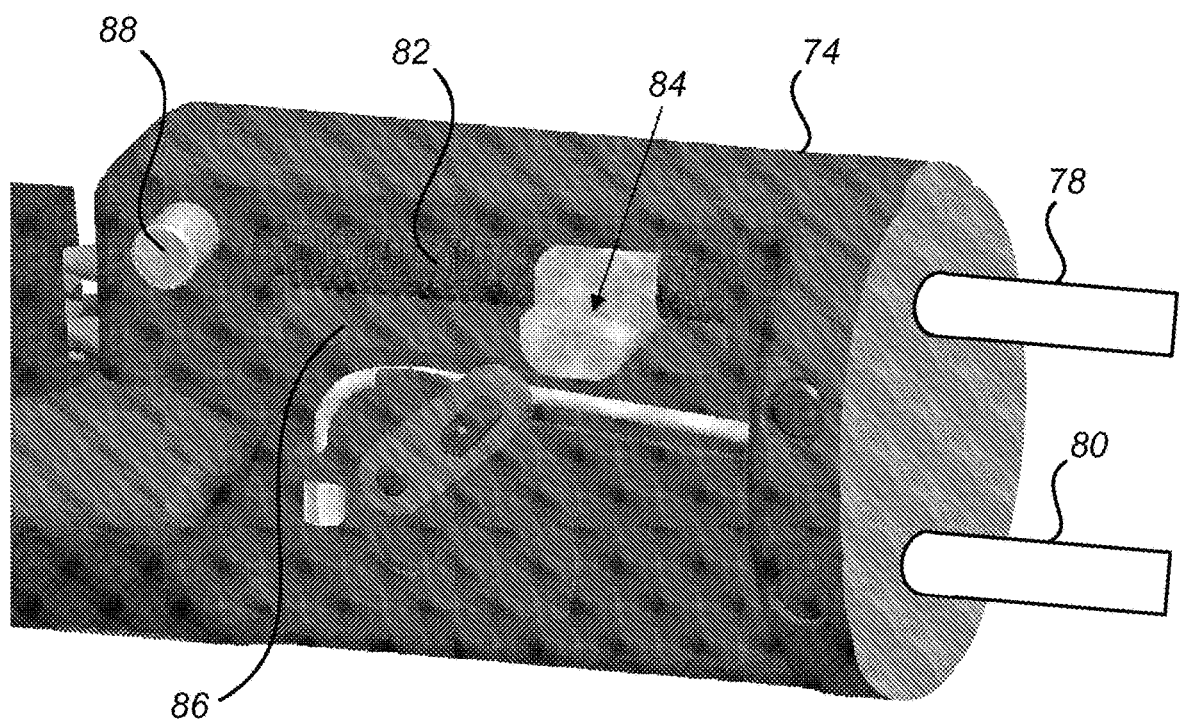
FIGS. 7A and 7B illustrate components of a lead screw actuation mechanism, in accordance with many embodiments.
Figure 7B:
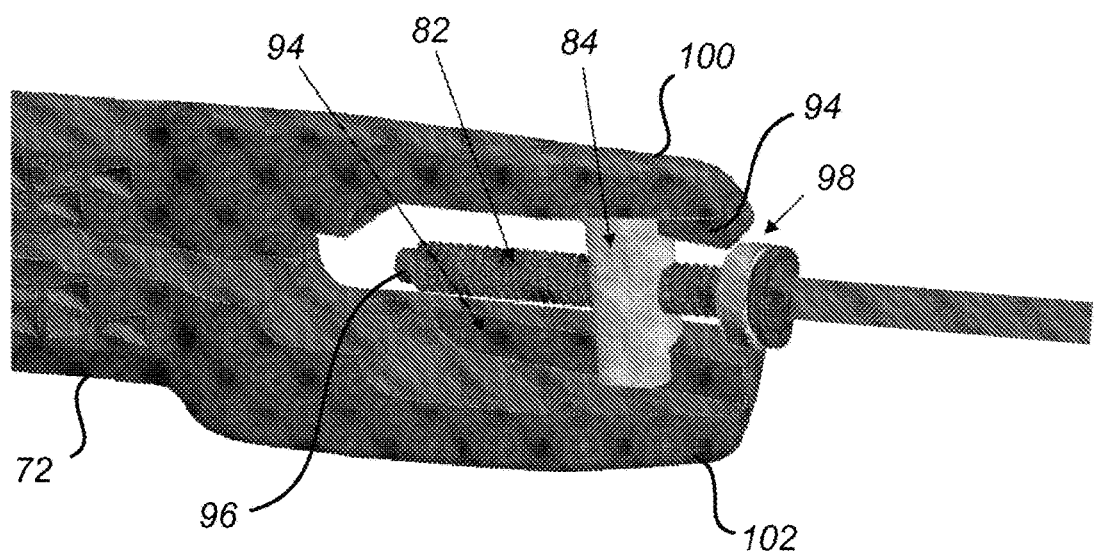
Figure 8A:
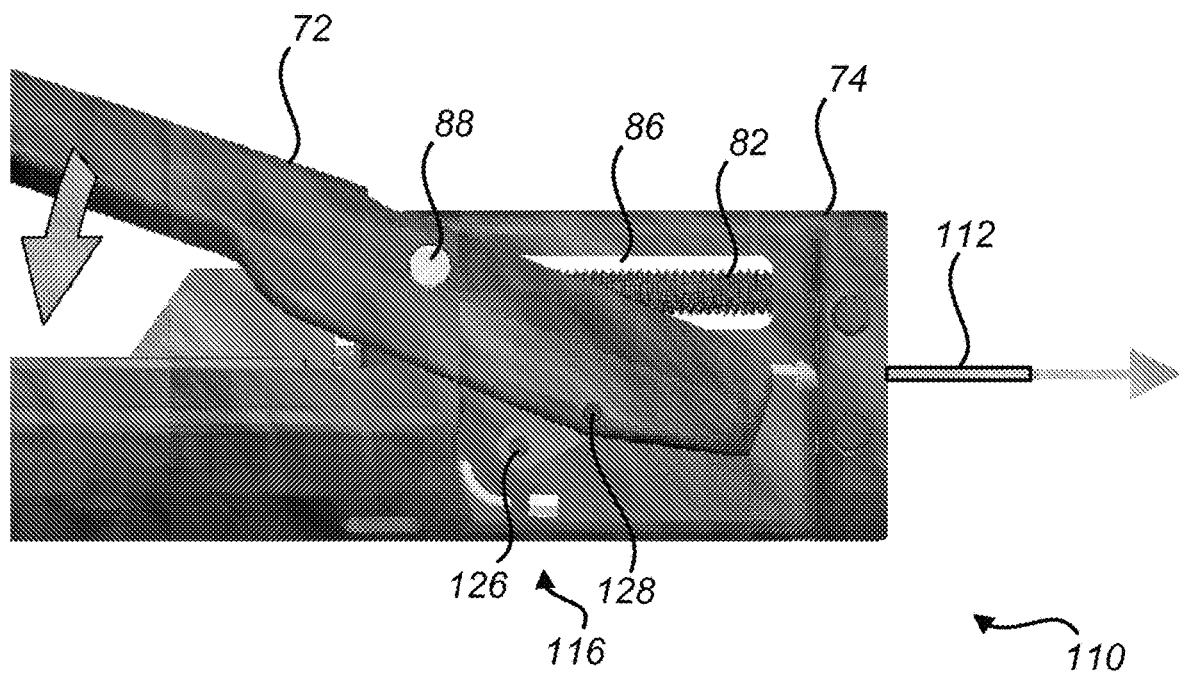
FIG. 8A illustrates components of a cable actuation mechanism, in accordance with many embodiments.
Figure 8B:
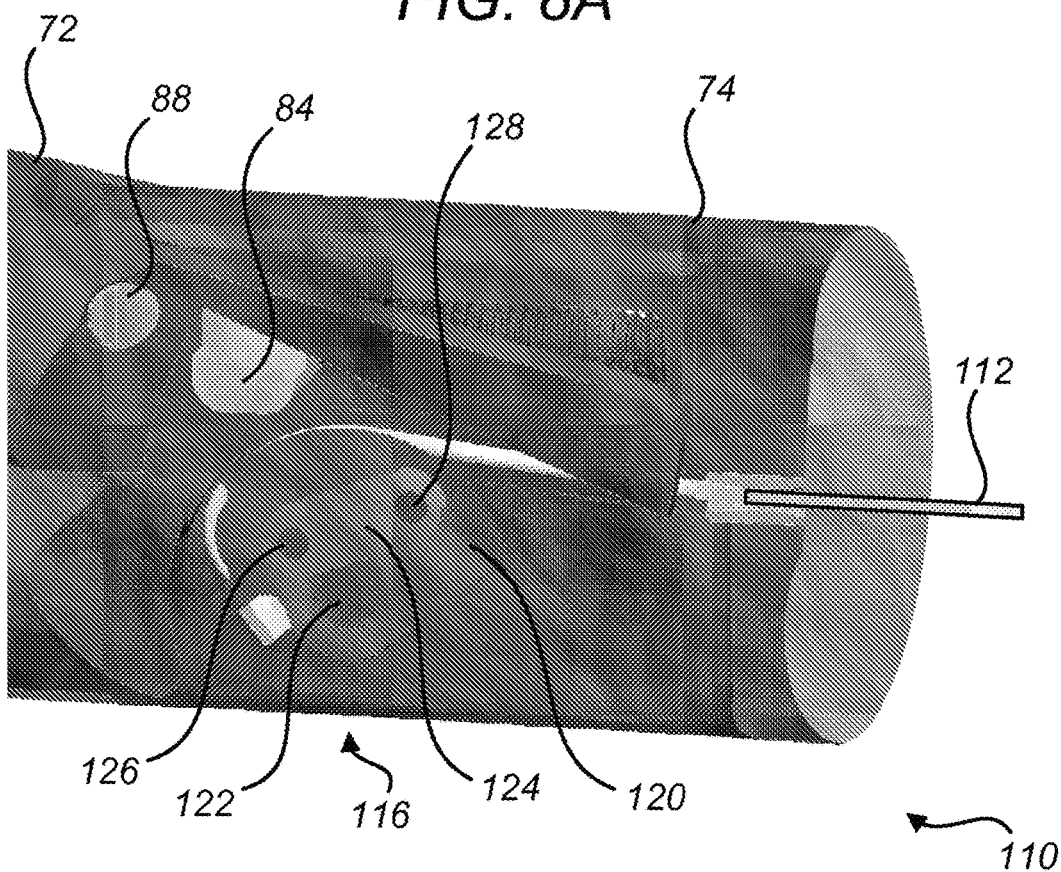
FIG. 8B is a perspective view of the end effector of FIG. 8A with a portion of the articulated jaw removed to show cable actuation mechanism components disposed behind the articulated jaw, in accordance with many embodiments.
Figure 8C:
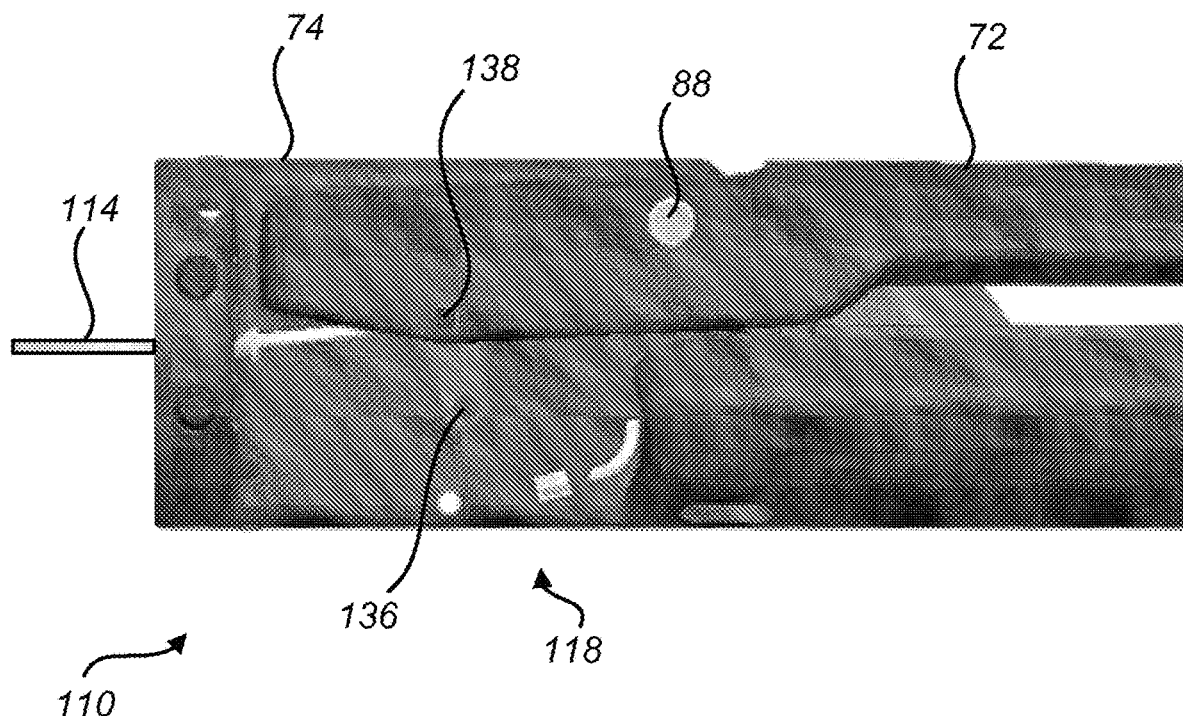
FIGS. 8C through 8F illustrate opposite side components of the cable actuation mechanism of FIG. 8A.
Figure 8D:
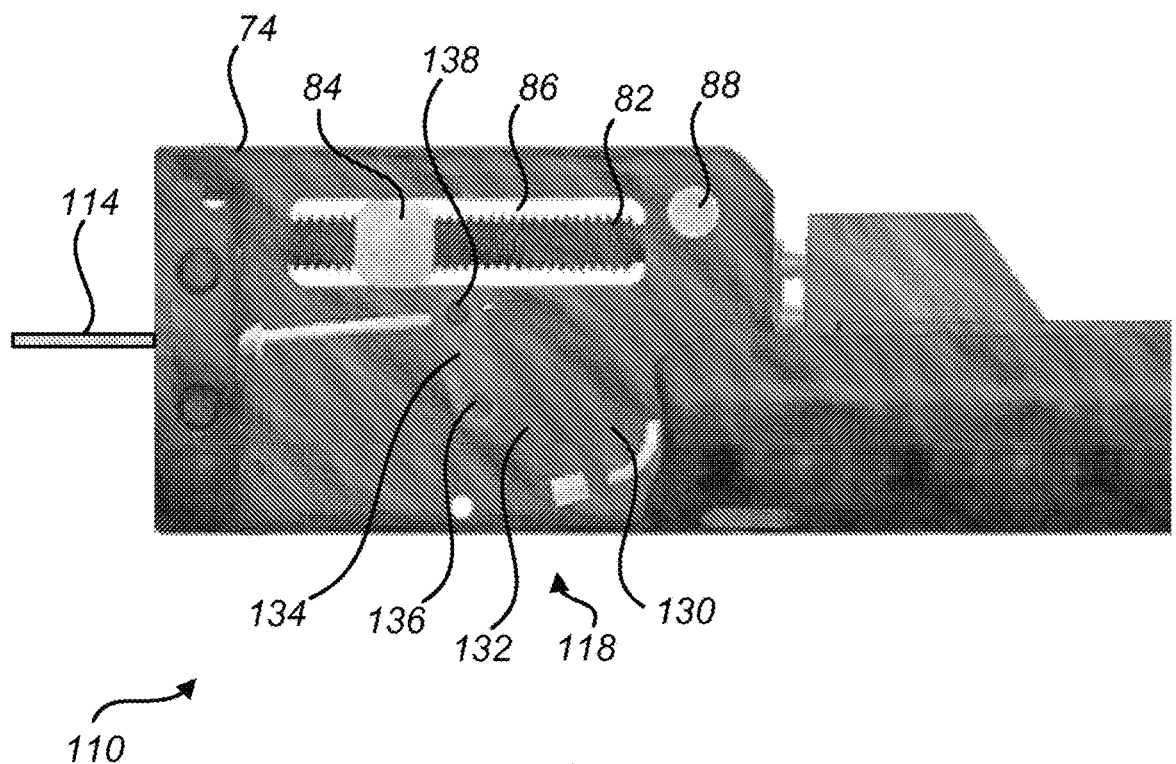
Figure 8E:
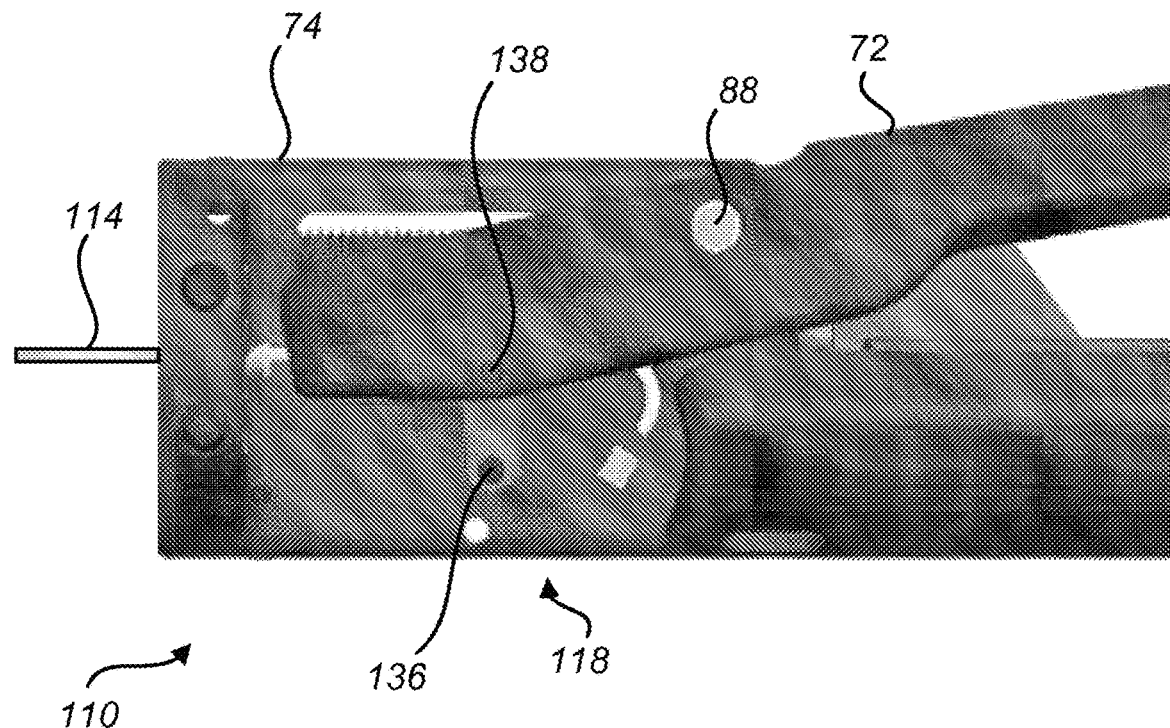
Figure 8F:
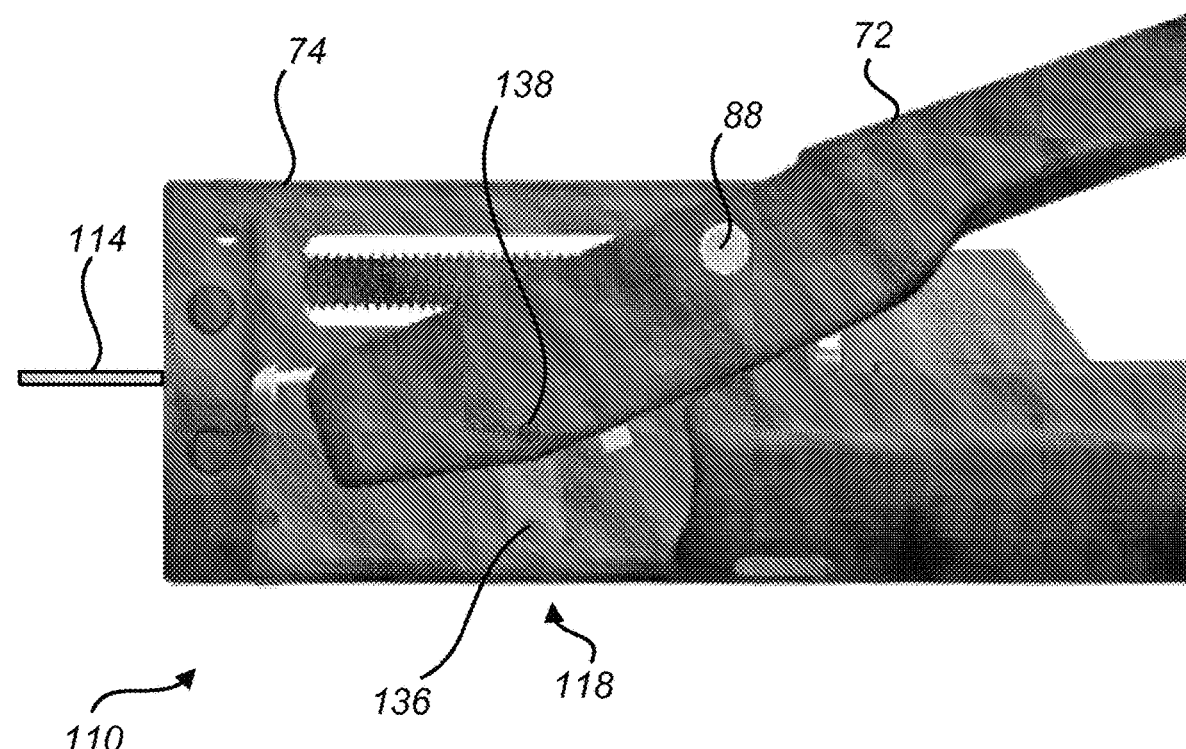

FIGS. 7A and 7B illustrate an example of a lead screw actuation mechanism to be used with an end effector having the structure shown in FIGS. 6A and 6B. The lead screw 82 has a distal journal surface 96 and a proximal journal surface that interfaces with a proximal bearing 98. In many embodiments, the distal journal surface 96 is received within a cylindrical receptacle located at the distal end of the cam slot 86. Such a distal support for the lead screw 82 can be configured to keep the lead screw 82 from swinging excessively, and with relatively large clearance(s) between the distal journal surface 96 and the cylindrical receptacle. The proximal bearing 98 is supported by the end effector base 74 so as to support the proximal end of the lead screw 82. The proximal bearing 98 can be a ball bearing, which may help to reduce friction and wear. A distal bearing (not shown) can be supported by the end effector base 74 so as to support the distal end of the lead screw 82, and the distal bearing can be a ball bearing. The lead screw driven cam 84 includes a threaded bore configured to mate with the external threads of the lead screw 82. The lead screw driven cam 84 includes top and bottom surfaces configured to interact with corresponding top and bottom surfaces of the cam slot 86. The interaction between lead screw driven cam 84 and the cam slot 86 prevents the lead screw driven cam 84 from rotating relative to the cam slot 86, which causes the lead screw driven cam 84 to translate along the cam slot 86 in response to rotation of the lead screw.

The articulated jaw 72 includes mating cam surfaces 94 that are configured so that the position of the lead screw driven cam 84 along the cam slot 86 determines the extent to which the rotational motion of the articulated jaw 72 around the pivot pin 88 is constrained by the lead screw driven cam 84. The articulated jaw 72 includes a first proximal side 100 and a second proximal side 102 that are separated by a central slot. The first and second proximal sides are disposed on opposing sides of the end effector base 74 when the articulated jaw 72 is coupled with the end effector base 74 via the pivot pin 88. Each of the first and second proximal sides 100, 102 includes a recessed area defining a mating cam surface 94 and providing clearance between the lead screw driven cam 84 and the proximal sides 100, 102. When the lead screw driven cam 84 is positioned at or near the proximal end of the cam slot 86 (near its position illustrated in FIGS. 7A and 7B), contact between the lead screw driven cam 84 and the mating cam surfaces 94 of the articulated jaw 72 hold the articulated jaw in a clamped configuration. When the lead screw driven cam 84 is positioned at the distal end of the cam slot 86, the rotational position of the articulated jaw around the pivot pin 88 is unconstrained by the lead screw driven cam 84 for a range of rotational positions between a clamped configuration (where there is a gap between the lead screw driven cam 84 and the mating cam surfaces 94 of the articulated jaw 72) and an open configuration (where there may or may not be a gap between the lead screw driven cam 84 and the mating cam surfaces 94 of the articulated jaw 72). For positions of the lead screw driven cam 84 in between the proximal and distal ends of the cam slot 86, the range of unconstrained motion can vary according to the cam surfaces used.

The use of a recess in each of the proximal sides 100, 102 to define the mating cam surfaces 94 of the articulated jaw 72 provides a number of benefits. For example, the use of recesses as opposed to traverse slots that extend through the proximal sides provides a continuous outside surface to the proximal sides 100, 102 of the articulated jaw, which is less likely to snag on patient tissue than would a traverse slot opening. The absence of traverse slots also helps to stiffen the proximal sides 100, 102 as compared to proximal sides with traverse slots, and therefore provides increased clamping stiffness. Such proximal sides 100, 102 may have increased stiffness in two planes, which may help maintain alignment of the articulated jaw 72 in the presences of external forces. Such increased stiffness in two planes may be beneficial in some surgical applications, for example, in tissue stapling where it is beneficial to maintain alignment between the staples and anvil pockets that form the staples. Further, the use of recesses instead of traverse slots also provides an actuation mechanism that is less likely to be jammed by extraneous material as compared to one having proximal sides with open traverse slots.

The lead screw actuation mechanism can be configured to provide a desired clamping force between the articulated jaw and an opposing jaw of the end effector to facilitate cutting or sealing of the tissue. For example, in many embodiments, the lead screw actuation mechanism is configured to provide at least 20 pounds of clamping force at the tip of the articulated jaw 72 (approximately 2 inches from the pivot pin 88). In many embodiments, the lead screw actuation mechanism is configured to provide at least 50 pounds of clamping force at the tip of the articulated jaw 72. In many embodiments, to produce 50 pounds of clamping force at the tip of the articulated jaw 72, the input torque to the lead screw 82 is approximately 0.1 Newton meters and the lead screw 82 has 33 turns. The system may detect the displacement of the motor, of the clamping or firing mechanism or the configuration of the end effector by sensing the displacement of the lead screw. For example, in many embodiments, the system is calibrated before starting the procedure so as to determine the range of motion of both the clamping and the firing mechanism and the displacement of the lead screw within that range of motion. Such calibration allows the system to determine the configuration of the end effector or the displacement of the mechanism solely from the displacement of the lead screw.

The lead screw actuation mechanism can be fabricated using available materials and components. For example, many components of the lead screw actuation mechanism can be fabricated from an available stainless steel). The lead screw driven cam 84 can be coated (e.g., TiN) to reduce friction against the surfaces it rubs against (e.g., lead screw 82; end effector base 74; proximal sides 100, 102 of the articulated jaw 72). Stranded cables can be used to drive the first actuation mechanism.

FIGS. 8A through 8F illustrate components of a cable actuation mechanism 110, in accordance with many embodiments. As described above, the lead screw driven cam 84 can be positioned at the distal end of the cam slot 86 (i.e., near the pivot pin 88). For such a distal position of the lead screw driven cam 84, as discussed above, the rotational position of the articulated jaw 72 about the pivot pin 88 is unconstrained for a range of rotational positions of the articulated jaw 72. Accordingly, the rotational position of the articulated jaw 72 about the pivot pin 88 can be controlled by the cable actuation mechanism 110. The cable actuation mechanism 110 is operable to vary the rotational position of the articulated jaw between the clamped configuration and the open configuration. The cable actuation mechanism 110 includes a pair of pull cables 112, 114. The cable actuation mechanism 110 also includes a first linkage 116 that is used to rotate the articulated jaw 72 about the pivot pin 88 towards the clamped configuration, and an analogous second linkage 118 that is used to rotate the articulated jaw 72 about the pivot pin 88 towards the open configuration. The first linkage 116 (shown in FIGS. 8A and 8B) includes a rotary link 120 that is mounted for rotation relative to the end effector base 74 via a pivot pin 122. A connecting link 124 couples the rotary link 120 to the articulated jaw 72 via a pivot pin 126 and a pivot pin 128. The first linkage 116 is articulated via a pulling motion of the pull cable 112. In operation, a pulling motion of the pull cable 112 rotates the rotary link 120 in a clockwise direction about the pivot pin 122. The resulting motion of the connecting link 124 rotates the articulated jaw 72 in a counter-clockwise direction about the pivot pin 88 towards the clamped configuration.

The second linkage 118 (shown in FIGS. 8C through 8F) of the cable actuation mechanism 110 includes analogous components to the first linkage 116, for example, a rotary link 130 mounted for rotation relative to the end effector base 74 via a pivot pin 132, and a connecting link 134 that couples the rotary link 130 to the articulated jaw 72 via two pivot pins 136, 138. The second linkage 118 is articulated via a pulling motion of the pull cable 114. The second linkage 118 is configured such that a pulling motion of the pull cable 114 rotates the articulated jaw 72 about the pivot pin 88 towards the open configuration. In many embodiments, the pivot pin 136 between the connecting link 134 and the rotary link 130 of the second linkage 118 is 180 degrees out of phase with the pivot pin 126 between the connecting link 124 and the rotary link 120 of the first linkage 116. Coordinated pulling and extension of the pull cables 112, 114 of the cable actuation mechanism 110 is used to articulate the articulated jaw 72 between the open and clamped configurations. In order to best provide equal and opposite cable motion (and thereby maintain cable tension in a capstan-driven system described below), a common rotational axis for the pivot pins 122, 132 is configured to lie on a plane that contains the rotational axes for pivot pins 128, 138 when the articulated jaw 72 is closed (or nearly closed) and again when the when the articulated jaw 72 is open (or nearly open). The connecting links 124, 134 are assembled symmetrically opposite about this same plane for the first and second linkages 116, 118. The distance between the pivot pins 122, 126 and between the pivot pins 132, 136 is the same for both the first and second linkages 116, 118, and the distance between the pivot pins 126, 128 and between the pivot pins 136, 138 is the same for both the first and second linkages 116, 118.

Figure 9A:
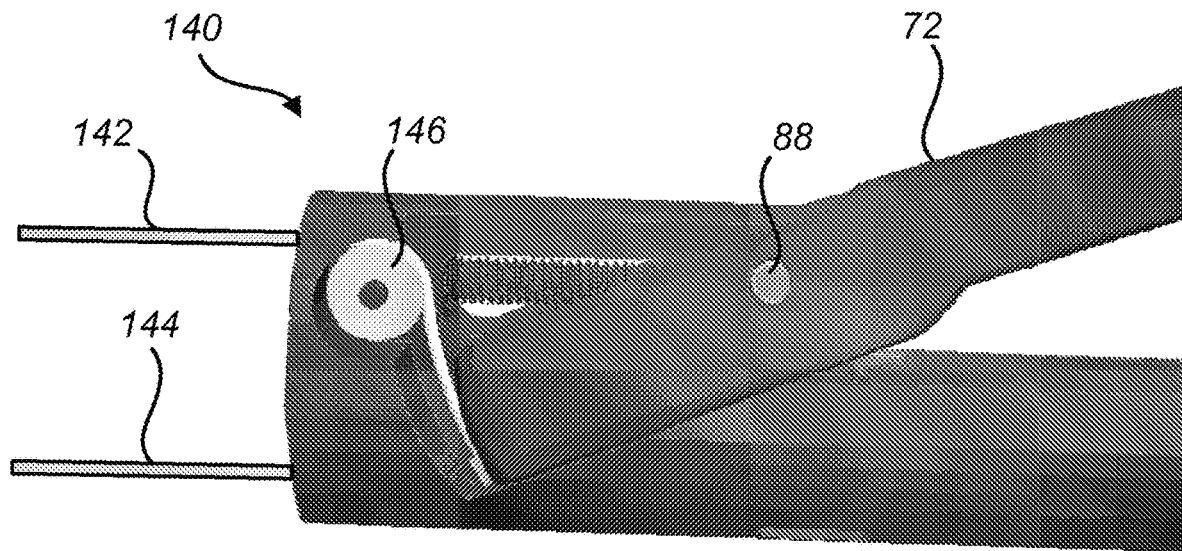
FIG. 9A is a perspective view illustrating a cable actuation mechanism, showing a cable used to articulate the jaw towards a clamped configuration, in accordance with many embodiments.
Figure 9B:
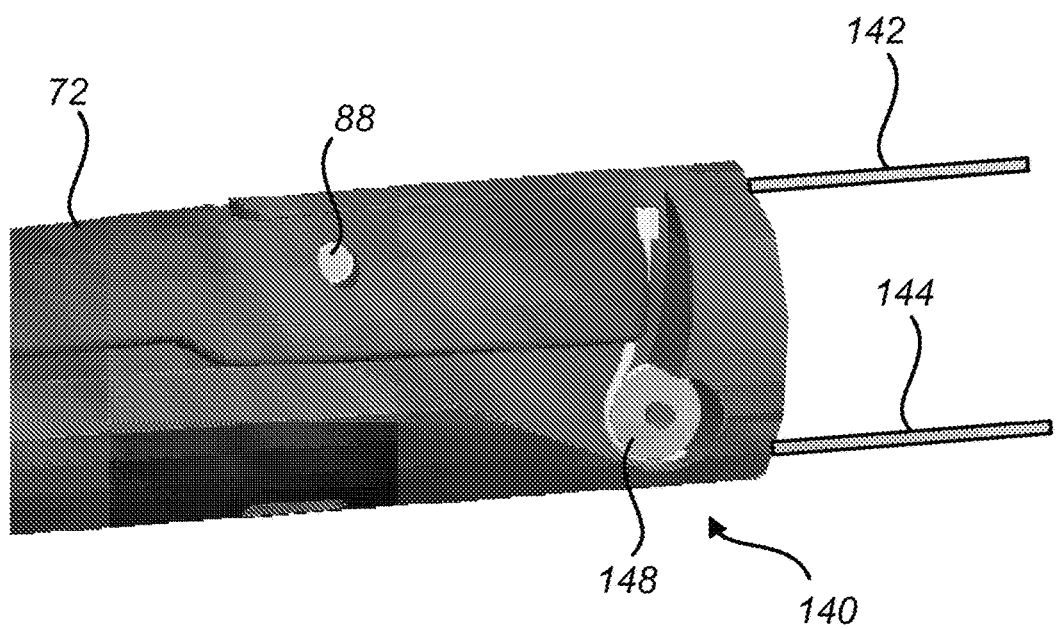
FIG. 9B is a perspective view illustrating the cable actuation mechanism of FIG. 9A, showing a cable used to articulate the jaw towards an open configuration.

FIGS. 9A and 9B illustrate an articulation of the articulated jaw 72 via another cable actuation mechanism 140, in accordance with many embodiments. In embodiment 140 of the cable actuation mechanism, a first pull cable 142 and a second pull cable 144 are directly coupled with the proximal end of the articulated jaw 72. The first pull cable 142 wraps around a first pulley 146 so that a pulling motion of the first pull cable 142 rotates the articulated jaw 72 about the pivot pin 88 towards the clamped configuration. The second pull cable 144 wraps around a second pulley 148 so that a pulling motion of the second pull cable 144 rotates the articulated jaw 72 about the pivot pin 88 towards the open configuration. Accordingly, coordinated pulling and extension of the first and second pull cables of the cable actuation mechanism 140 is used to articulate the articulated jaw 72 between the open and clamped configurations. In order to best provide equal and opposite cable motion (and thereby maintain cable tension in the capstan-driven system described below), the radius of the arc prescribed by cable 142 about the pivot 88 is substantially the same as the radius prescribed by cable 144 about the pivot 88.

Although the mechanisms may comprise lead screws, cables, or hypotubes, alternate mechanisms can be used to effect clamping or staple firing. For example, an actuation mechanism comprising push/pull rods or springs can be used.

Figure 10:
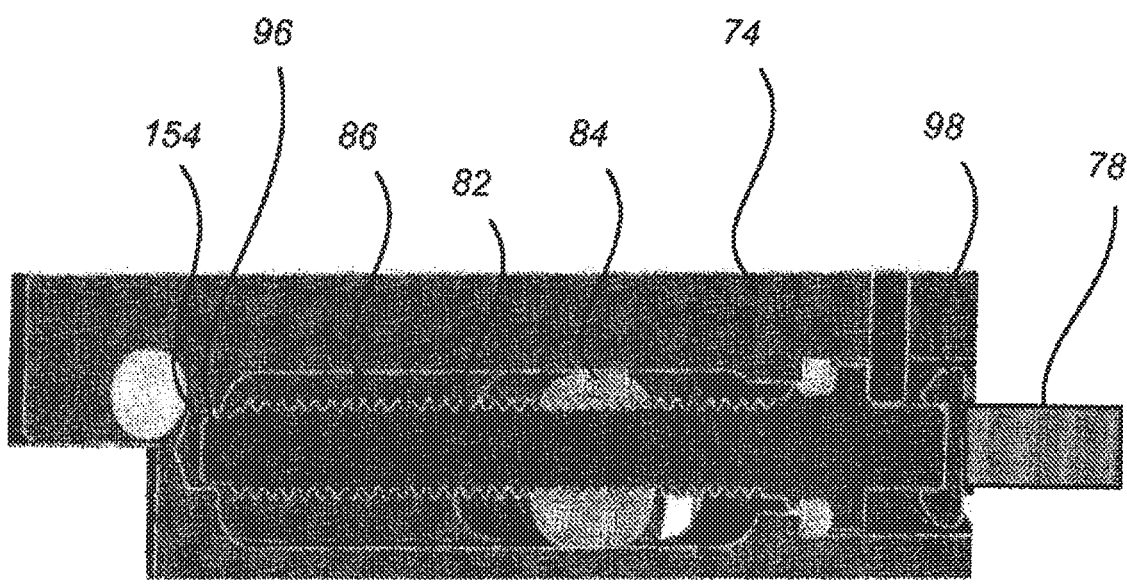
FIG. 10 is a cross-sectional view illustrating components of a lead screw actuation mechanism, in accordance with many embodiments.

FIG. 10 is a cross-sectional view illustrating components of the above discussed lead screw actuation mechanism. The illustrated components include the lead screw 82, the lead screw driven cam 84, the cam slot 86 in the end effector base 74, the distal journal surface 96, the cylindrical receptacle 154 in the end effector base, and the proximal bearing 98 supported by the end effector base 74.

Figure 11:
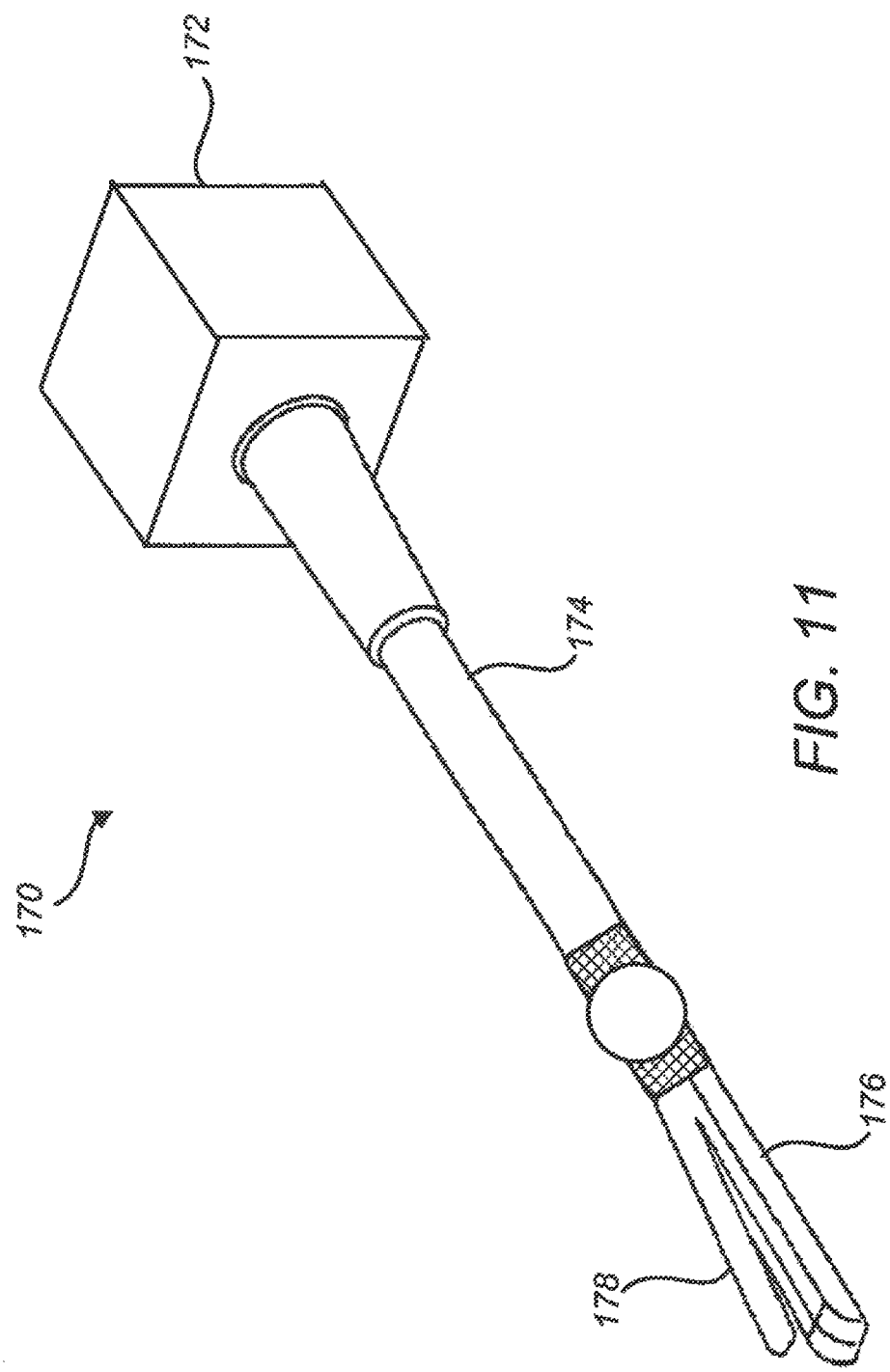
FIG. 11 is a simplified diagrammatic illustration of a tool assembly, in accordance with many embodiments.

FIG. 11 is a simplified diagrammatic illustration of a tool assembly 170, in accordance with many embodiments. The tool assembly 170 includes a proximal actuation mechanism 172, an elongate shaft 174 having a proximal end and a distal end, a tool body 176 disposed at the distal end of the shaft, a jaw 178 movable relative to the tool body 176 between a clamped configuration and an open configuration, a first actuation mechanism coupled with the jaw, and a second actuation mechanism coupled with the jaw. The first actuation mechanism is operable to vary the position of the jaw relative to the tool body between the clamped configuration and the open configuration. The second actuation mechanism has a first configuration where the jaw is held in the clamped configuration and a second configuration where the position of the jaw relative to the tool body is unconstrained by the second actuation mechanism. The first actuation mechanism is operatively coupled with the proximal actuation mechanism. In many embodiments, the first actuation mechanism comprises a pair of pull cables that are actuated by the proximal actuation mechanism. The second actuation mechanism is operatively coupled with the proximal actuation mechanism. In many embodiments, the second actuation mechanism includes a lead screw driven cam located in the tool body that is driven by the proximal actuation mechanism via a drive shaft extending through the elongate shaft 174 from the proximal actuation mechanism.

The tool assembly 170 can be configured for use in a variety of applications. For example, the tool assembly 170 can be configured as a hand held device with manual and/or automated actuation used in the proximal actuation mechanism. The tool assembly 170 can also be configured for use in surgical applications, for example, electrocautery sealing, stapling, etc. The tool assembly 170 can have applications beyond minimally invasive robotic surgery, for example, non-robotic minimally invasive surgery, non-minimally invasive robotic surgery, non-robotic non-minimally invasive surgery, as well as other applications where the use of the disclosed redundant jaw actuation would be beneficial.

Figure 12:
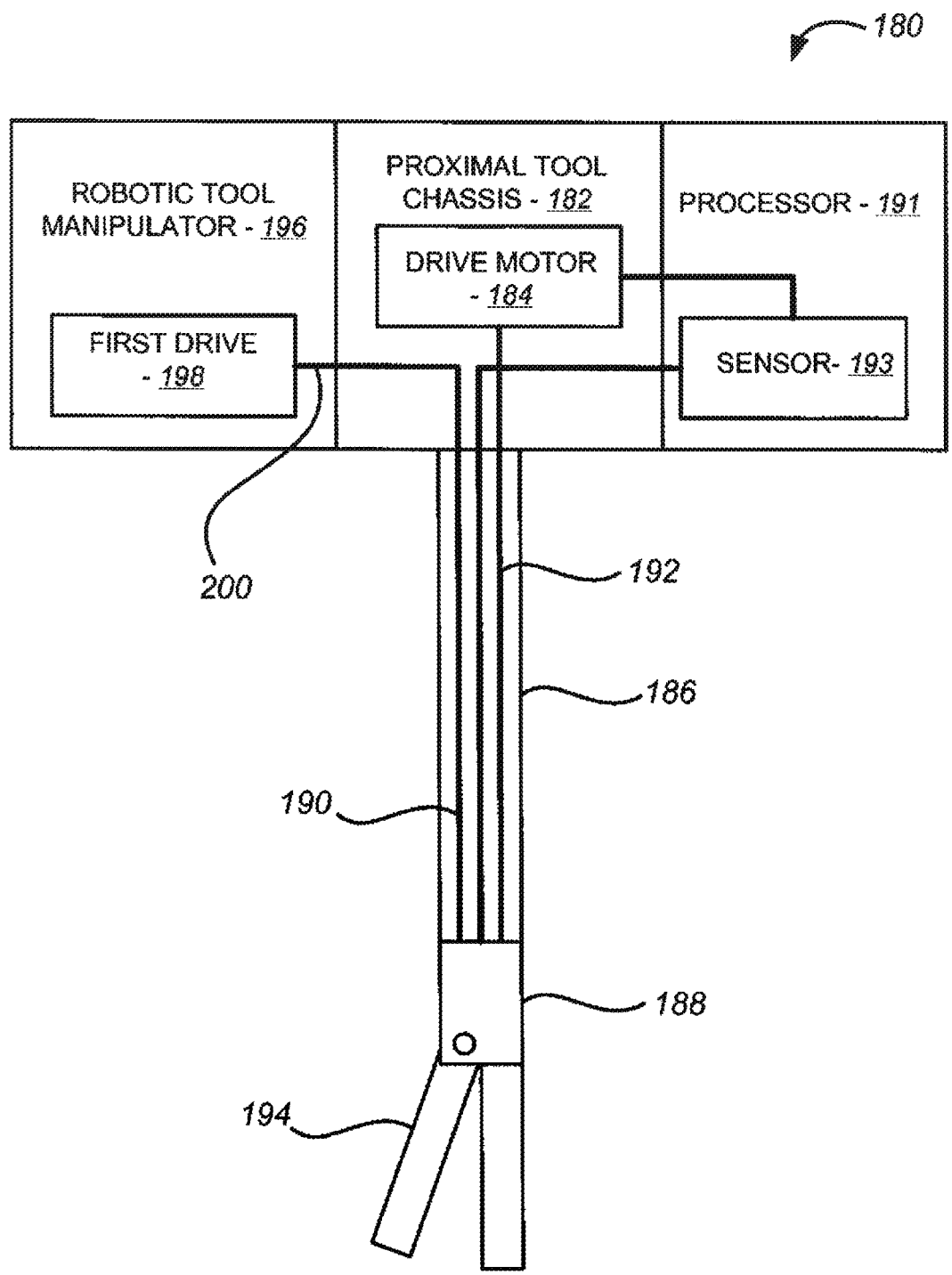
FIG. 12 is a simplified diagrammatic illustration of a robotic tool mounted to a robotic tool manipulator, in accordance with many embodiments.

Redundant jaw actuation can be used to articulate a jaw of a robotic tool end effector. For example, FIG. 12 schematically illustrates a robotic tool 180 employing redundant jaw actuation. The robotic tool 180 includes a proximal tool chassis 182, a drive motor 184, an instrument shaft 186, a distal end effector 188, a first actuation mechanism portion 190, and a second actuation mechanism 192. The distal end effector 188 comprises an articulated jaw 194. The proximal tool chassis 182 is releasably mountable to a robotic tool manipulator 196 having a first drive 198, and a first actuation mechanism portion 200 that operatively couples with the first actuation mechanism portion 190 of the robotic tool 180 when the proximal tool chassis 182 is mounted to the robotic tool manipulator 196. The instrument shaft 186 has a proximal end adjacent the tool chassis 182, and a distal end adjacent the end effector 188. The first actuation mechanism (comprising portion 200 and portion 190) couples the first drive 198 to the articulated jaw 194 when the tool chassis 182 is mounted to the tool manipulator 196 so as to articulate the end effector 188 between an open configuration and a clamped configuration. The second actuation mechanism 192 couples the drive motor 184 to the articulated jaw 194 so as to apply a firing force to a staple so as to fire the staple from the end effector through the tissue clamped within the jaws of the end effector. The first actuation mechanism can be a lead screw-driven mechanism that provides relatively high forces so as to fire the staple through the tissue. The second actuation mechanism can include a drive shaft that couples the drive motor 184 with a lead screw actuation mechanism, for example, an above discussed lead screw actuation mechanism that provides the high clamping force mode. System 180 includes Sensor 193 for monitoring the drive parameters of the first drive 198 and the drive motor 184 during clamping and firing, respectively. Sensor 193 may also detect the displacement of the first drive and the drive motor so as to determine the acceptable range of desired drive parameters according to a given displacement of the motor or configuration of the end effector. The configurations of the end effector in a clamping mode may include an open configuration, a close/clamped configuration and any configuration therebetween. The configurations of the end effector in the firing mode may include a pre-firing configuration in which one or more staples are disposed within the end effector and releasably coupled with the drive motor 184 through a mechanism and a post-firing configuration where one or more staples have been fired through the tissue, and typically bent so as to seal the tissue, the staple having been released from the end effector. The configurations of the end effector may also include any configuration in between the pre-firing and post-firing mode. By detecting the displacement of the first drive or drive motor, the sensor can determine a given configuration of the end effector in either mode, so as to more accurately determine the acceptable range of driving parameters and predict failure of clamping or firing.

In accordance with the present teachings, the firing force for forming staples is approximately 1.5-2.0 pounds, however, the staple cartridge construction allows between two (2) and (6) staples to be fired (and in doing so, causing them to be formed) simultaneously. Thus, for a staple cartridge intended to fire two (2) staples, an expected actuation/firing force would be approximately 3.0-4.0 pounds, while for a staple cartridge intended to fire six (6) staples at a time, the expected initial actuation/firing force to be approximately 9-12 pounds. (It should be noted that these forces are approximate and are not indicative of the input force which may be delivered via any number of mechanical means, i.e. linear motion (push/pull), rotary motion, etc.) In a case where, during initial actuation of the firing sequence staples are not being formed due to staples missing from a staple cartridge, the initial actuation force required would be low because it would move only the drive member (staples would not be encountered, pushed, and formed) through the cartridge, requiring a force of about less than 1 pound. Such an initial actuation force would be significantly lower than the expected value of about 4 pounds or about 10 pounds (depending on cartridge size and type), and when a force lower than the expected minimum (minimum threshold) is sensed, the Processor would identify the low force as a stapler misfire or failure. As discussed below, the Processor may, in such a case, terminate a stapling sequence, and may further provide a warning to the user of the misfire or failure.

Continued monitoring of the staple actuation force after initial actuation would consider whether the actuation force remains within an acceptable range of forces, with a lower end of the range indicating an empty cartridge and an upper end of the range representing a potentially jammed stapler or a stapler encounter a material too tough to be stapled. During the continued monitoring phase, the Processor would identify potential problems with the stapling sequence if the actuation force fell below a minimum force of approximately 2 pounds or 5 pounds, depending on the size and type of the staple cartridge, or if the actuation force exceeded a maximum force (maximum threshold) of approximately 6-8 pounds or 15-20 pounds, depending on the size and type of the staple cartridge.

According to an exemplary embodiment of the present teachings, the Processor continuously compares a measured actuation force applied to the staple cartridge (Tmeas) to a minimum threshold force (Tmin) and a maximum threshold force (Tmax) throughout the staple firing sequence. FIG. 16C illustrates an exemplary measured actuation force, or torque, applied to a staple cartridge during a successful staple firing sequence. As illustrated, the measured torque Tmeas remains above the minimum threshold force Tmin and below the maximum threshold force Tmax.

Figure 13:
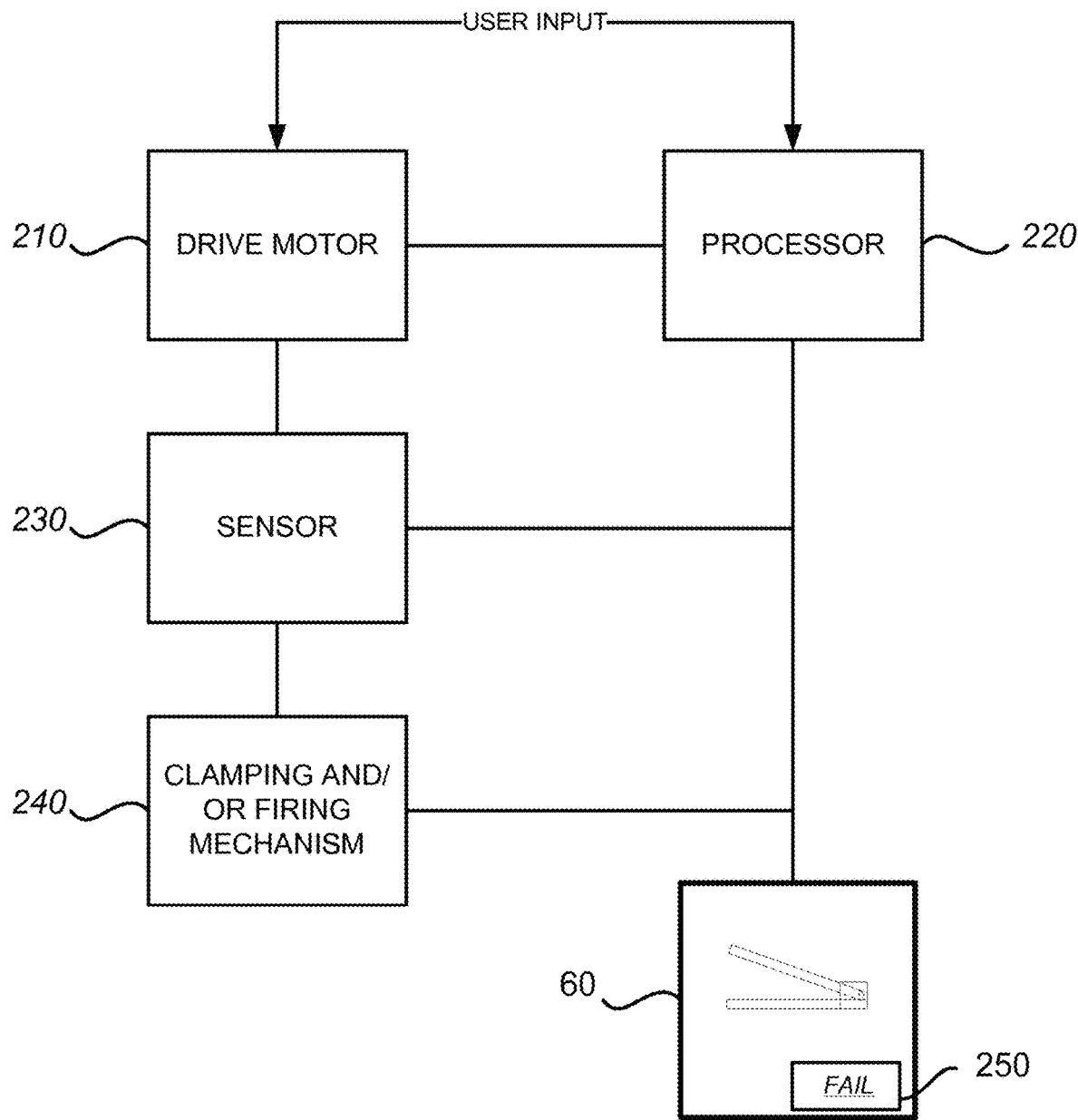
FIG. 13 is a diagrammatic view of a telerobotic surgical system, in accordance with many embodiments.

FIG. 13 is a diagrammatic view of a telerobotic surgical system which incorporates an embodiment of the present teachings. In the example of FIG. 13, a physician inputs a command to the system to clamp a tissue or fire a staple. In response to the user command, the system begins driving the motor 210 so as to drive clamping or firing through the clamping and/or firing mechanism 240. As mechanism 240 effects clamping or firing, Processor 220 monitors a drive parameter, such a torque output, of Motor 210. Monitoring may comprise comparing the torque output to an acceptable range of torque outputs for a given displacement and/or velocity of the motor or mechanism. The Processor 220 may be coupled to any or all of the Motor 210, the Mechanism 240 or a Sensor 230 for detecting a displacement of the motor or mechanism during the clamping or firing. In response to the monitored drive parameter falling outside an acceptable range of torque outputs (or displacements of the driving mechanism), Processor 220 outputs a Failure Indication 250 on Display 60 of the user interface, indicating that clamping or firing has failed, or a likelihood of failure. Typically, Display 60 includes images of the end effector during clamping or firing.

In an exemplary embodiment, Processor 220 may run an algorithm, stored on a memory or other computer-readable storage medium (not shown) that monitors the firing force or torque applied by the telerobotic surgical system. The Processor 220 will stop the staple firing sequence if the firing force or torque is below a threshold force value, indicative of cartridge misfire or the failure to deploy staples. Similarly, the Processor 220 will stop the staple firing sequence if the firing force or torque is above a second threshold force value, indicative of jamming in the stapler. By monitoring the firing force, and most particularly an initial firing force, Processor 220 may be able to prevent tissue damage. For example, when a firing force is indicative of failure to deploy staples, terminating the firing sequence will reduce the possibility that unstapled tissue will be cut by a knife deployed by the staple cartridge. At the beginning of a cutting sequence, there may be a slight delay between the time the stapler deploys staples and the knife blade begins to cut the stapled tissue. This delay may be attributable to the time necessary to form staples before stapling the tissue. Once there is an indication that a force necessary to properly form and deploy staples is not present, Processor 220 aborts the firing and cutting sequence. Although discussed with respect to the initiation of a firing and cutting sequence, Processor 220 may monitor the firing force throughout an entire firing and cutting sequence, and control the process by terminating the process if the firing force drops below the first threshold value or rises above the second threshold value.

Processor 220 receives a signal indicative of an initial actuation force applied to staple cartridge 76. Processor 220 compares the initial actuation force to a threshold value, for example a lower threshold value, and controls the firing and cutting sequence based on the comparison. If the initial action force is less than the lower threshold value, then the Processor 220 terminates the staple firing and cutting sequence. An initial actuation force less than the lower threshold value is indicative that staples are not being formed or deployed properly, and termination of the sequence may prevent tissue damage in the form of tissue being cut without first being stapled. If the actuation force is greater than the lower threshold value, then Processor 220 may permit the firing and cutting sequence to continue. Processor 220 may continue to monitor and the actuation force applied to the staple cartridge and compare the actuation force to the lower threshold value and also to an upper threshold value. If the actuation force is greater than the upper threshold value, Processor 220 may terminate the firing and cutting sequence. An actuation force greater than the upper threshold value is indicative of a jam in the staple firing mechanism, and termination of the sequence can prevent burnout of the motor or other problems with the instrument, as well as prevent tissue damage. Processor 220 may output to a user interface an indication of determinations to terminate the firing and cutting sequence or to permit the sequence to continue. Such outputs to the user interface may take the form of warnings to the user, as discussed below.

Figure 14A:
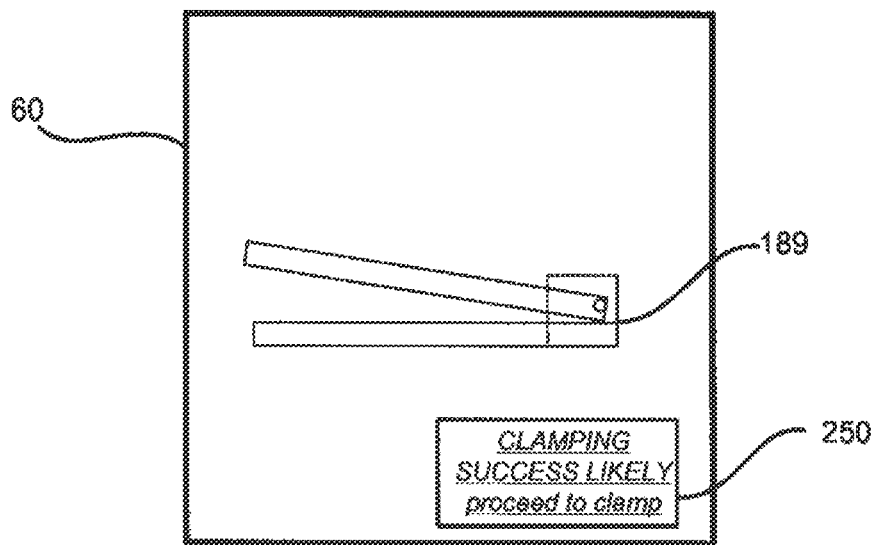
FIGS. 14A-14B illustrate the user interface assembly having a clamping failure indicator, in accordance with many embodiments.
Figure 14B:
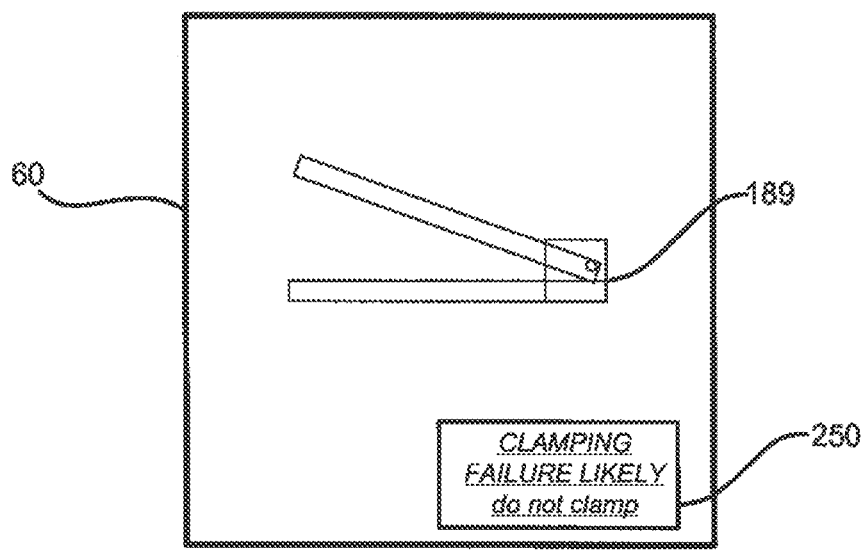

FIGS. 14A-14B illustrate two examples of failure indicator 250 that may appear on Display 60 of System 10. Typically, the user interface Display 60 depicts images and/or visual representations of the surgical tool end effectors during the surgery in addition to the indicators of clamping or firing failure. The failure indicator may be superimposed over the images on the user interface display during the surgical procedure so as to seamlessly incorporate the features of the present teachings into the surgical procedure. Preferably, the failure indicator only appears when the Surgeon has commanded System 10 to clamp or fire a staple into a clamped tissue. By monitoring the drive parameter, System 10 provides an indication of failure during the procedure. FIG. 14A depicts Display 60 with a clamping failure indicator 250 superimposed on the lower right area of the screen, wherein the failure indicator 250 indicates that clamping success is likely and that the system is proceeding to clamp. FIG. 14B depicts Display 60 with failure indicator 250 superimposed on the lower right area of the screen, wherein the indicator indicates that clamping will likely fail. Failure indicator 250 is output in response to the monitored drive parameter driving the clamping being outside the predetermined range of acceptable drive parameters.

Figure 15A:
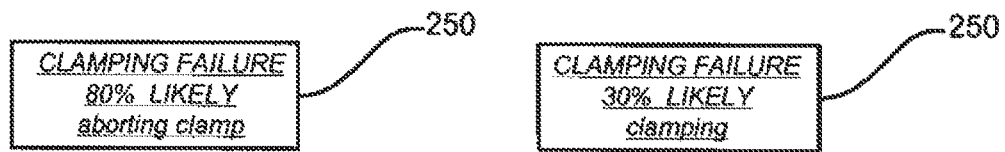
FIGS. 15A-15B illustrate examples of indicators of clamping failure indicators, in accordance with many embodiments.
Figure 15B:
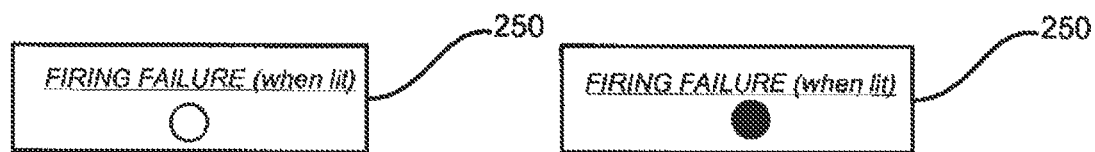

FIG. 15A-15B illustrate additional examples of the clamping prediction indicator 250. FIG. 15A depicts an example of a failure indicator showing a likelihood of clamping failure as a gradient, where in this example, the likelihood is expressed as a percentage of chance. For example, the further outside the range of predetermined drive parameters the actual monitored drive parameter is, the more likely clamping failure will be. For example, in one embodiment, if the actual monitored driving torque is within 5% of a predetermined target driving torque, the system will display an indicator of 90% likelihood of clamping success. As the monitored driving torque further diverges from the target driving torque, the likelihood decreases in a monotonic relationship, such as from 90% down to a 0% likelihood of clamping. Alternatively, the driving parameter may be the displacement of the driving mechanism. In such an embodiment, the system may monitor the displacement of the driving mechanism and indicate clamping or firing failure when the displacement is outside a predetermined range of acceptable displacements. FIG. 15B depicts an embodiment having an indicator which toggles between two settings. When the light of the indicator is lit, likely firing failure is indicated, otherwise firing failure is not indicated.

Figure 16A:
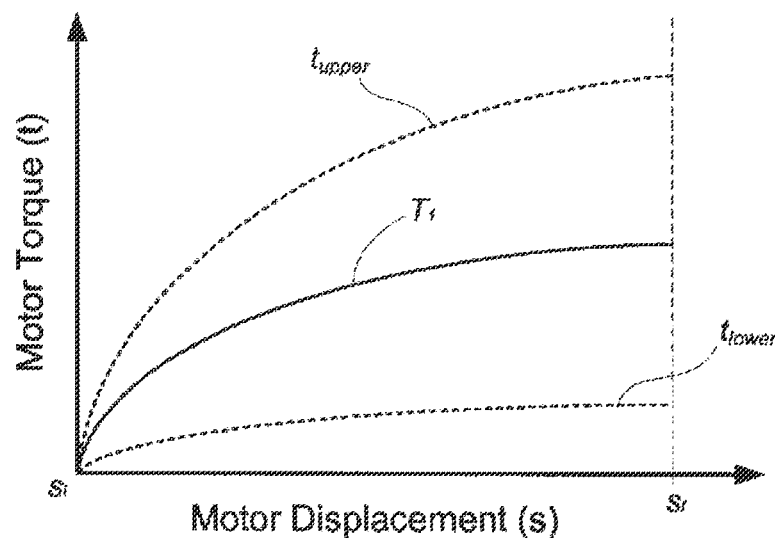
FIGS. 16A-16B illustrates exemplary motor torques during clamping as compared to a range of acceptable motor torques which vary with motor displacement, in accordance with many embodiments.
Figure 16B:
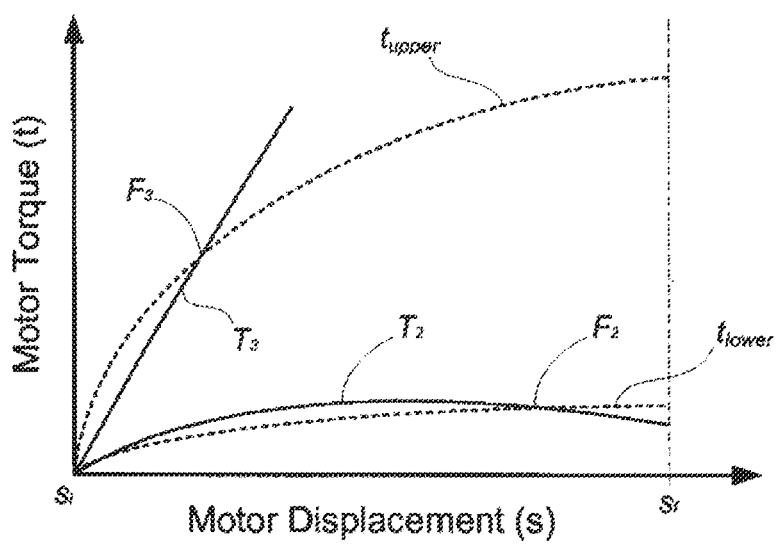
Figure 16C:
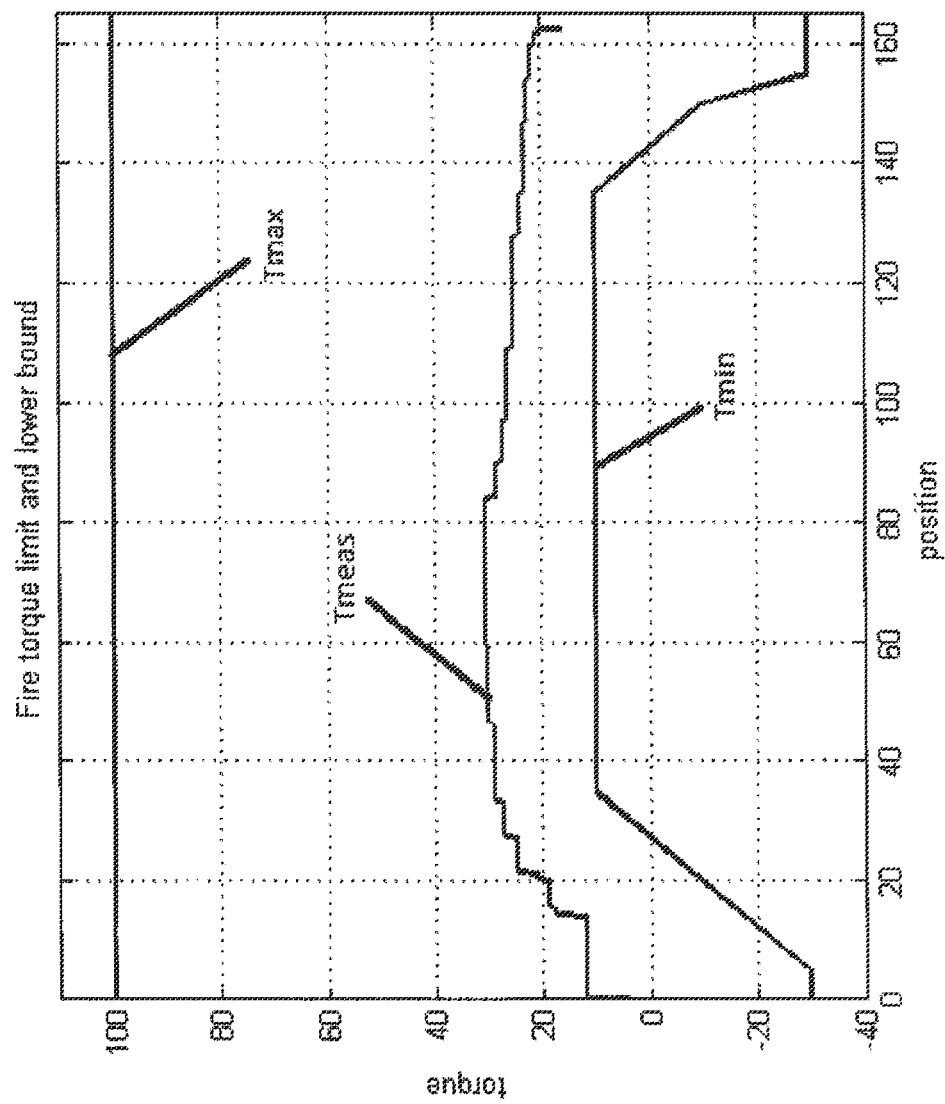
FIG. 16C illustrates exemplary minimum and maximum threshold torques compared to a measured actuation torque during a staple firing sequence, in accordance with the present teachings.

FIGS. 16A-16C illustrate graphs of a monitored drive parameter in relation to an acceptable range of desired drive parameters, in accordance with many exemplary embodiments of the present teachings. This embodiment illustrates that the system may provide an indication of clamping and/or firing failure simply from monitoring the torque of the motor as it drives the clamping or firing of the system. As shown, the predetermined range of torques may vary in relation to the displacement of the motor as it effects movement of the end effector. The displacement (s) of the motor may be correlated by the system to a position of the end effector during the clamping process. For example, during clamping, as the displacement of the motor moves from $S_i$ to $S_f$, the jaws of the end effector move from an open configuration to a closed (clamped) configuration. Similarly, the motor displacement may be used to track the position or configuration of the end effector during firing of a staple into the clamped tissue. In many embodiments, before performing a procedure, the system calibrates the jaws of the end effector from a first to a second configuration, such as calibrating jaws from an open position to a closed position, so as to correlate the displacement of the motor with the configuration of the end effector.

FIG. 16A illustrates a predetermined range of acceptable driving torques (t) which vary with motor displacement(s). The range is delimited by two functions, an upper boundary $t_{upper}$ and a lower boundary $t_{lower}$. The system outputs an indication of clamping failure in response to the monitored driving torque T as compared to the predetermined range of acceptable driving torques. If the displacement of the motor reaches $S_f$ and the system has not indicated likely clamping or firing failure, the system may provide an indication of successful clamping or firing. In this example, the graph depicts the acceptable range of torques and the monitored driving torque during clamping as T1. As shown, during the clamping, T1 remains within the acceptable range of driving torques, thus the system would output an indication that clamping is likely successful (which may include a lack of an indication of failure).

FIG. 16B illustrates a similar predetermined range of acceptable driving torques (t) and two separate driving torques, T2 and T3 (occurring at different times). As shown, T2 falls below the lower boundary, $t_{lower}$, of the acceptable range of torques. This may occur where the tissue has slipped out of the jaws of the end effector and less torque is required to close the jaws since there is no tissue between the jaws. Alternatively, this situation may occur, for example, where the cartridge does not include staples (e.g., a previously used cartridge is loaded in the stapler) or is missing other items. In such case, the system would output an indication of likely clamping failure at Failure Point F2, at which point the system may suspend driving of the clamping to prevent any possible tissue damage from continuing to apply the clamping force after failure occurs. Failure may also occur if the driving torque exceeds the upper boundary of the range of acceptable torques, as shown by monitored torque T3. This may occur where jaws have clamped onto a bone and an excessive amount of torque is required to reach the closed/clamped configuration, which may potentially cause tissue damage to the bone or surrounding tissue. This might also occur when a staple is jammed. In this example, the monitored torque exceeds $t_{upper}$ at Failure Point F3, at which point the system may suspend driving of the clamping or firing to reduce the likelihood of tissue damage. In response to detection of failure, the system may suspend driving of the drive parameter or reverse the driving force to unclamp the tissue, in addition to providing an indication of failure.

FIG. 16C illustrates a predetermined range of acceptable driving torques (t) which vary with motor displacement(s). The range is delimited by two functions, an upper boundary Tmax and a lower boundary Tmin. The system outputs an indication of firing failure in response to the monitored driving torque Tmeas as compared to the predetermined range of acceptable driving torques. In this example, the graph depicts the acceptable range of torques and the monitored driving torque during firing as Tmeas. As shown, during the firing, Tmeas remains within the acceptable range of driving torques, thus the system would output an indication that firing is likely successful (which may include a lack of an indication of failure).

Figure 17:
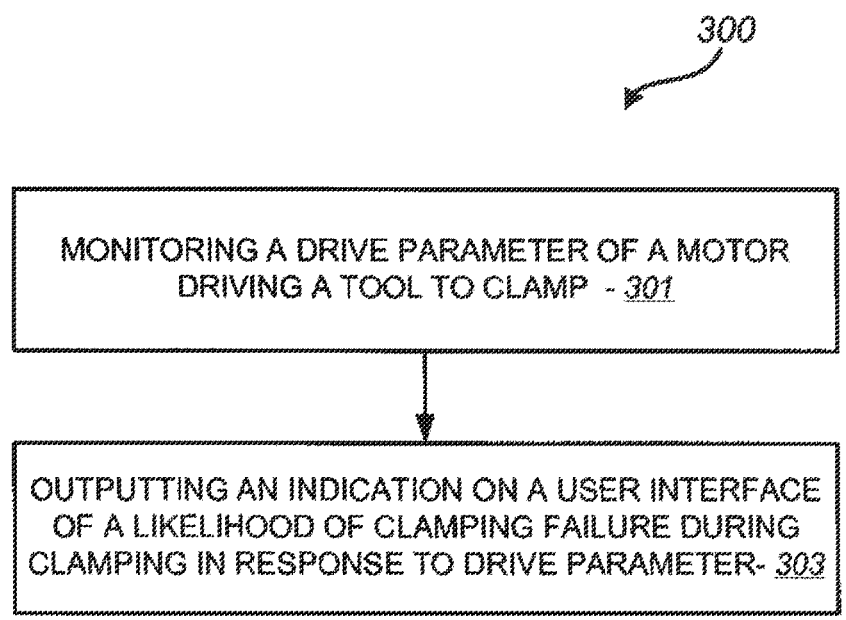
FIGS. 17-20 illustrate methods, in accordance with many embodiments.
Figure 18:
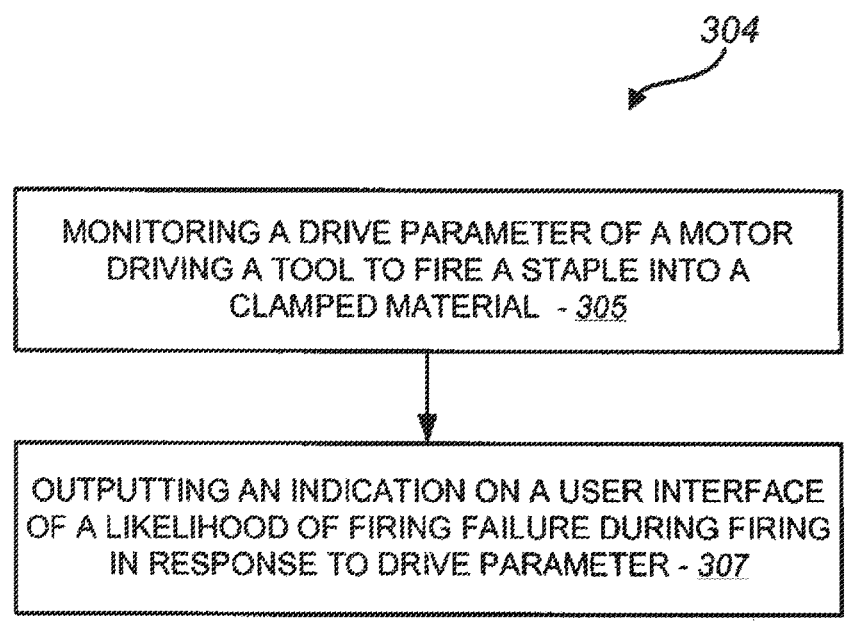
Figure 19:
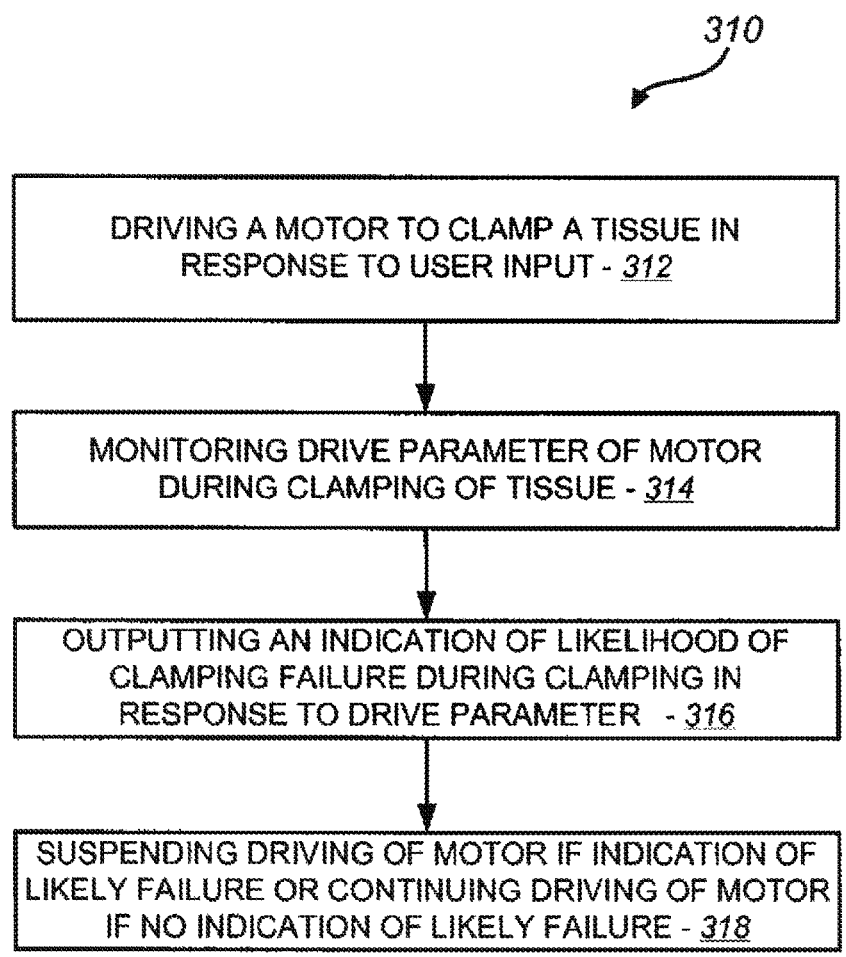
Figure 20:
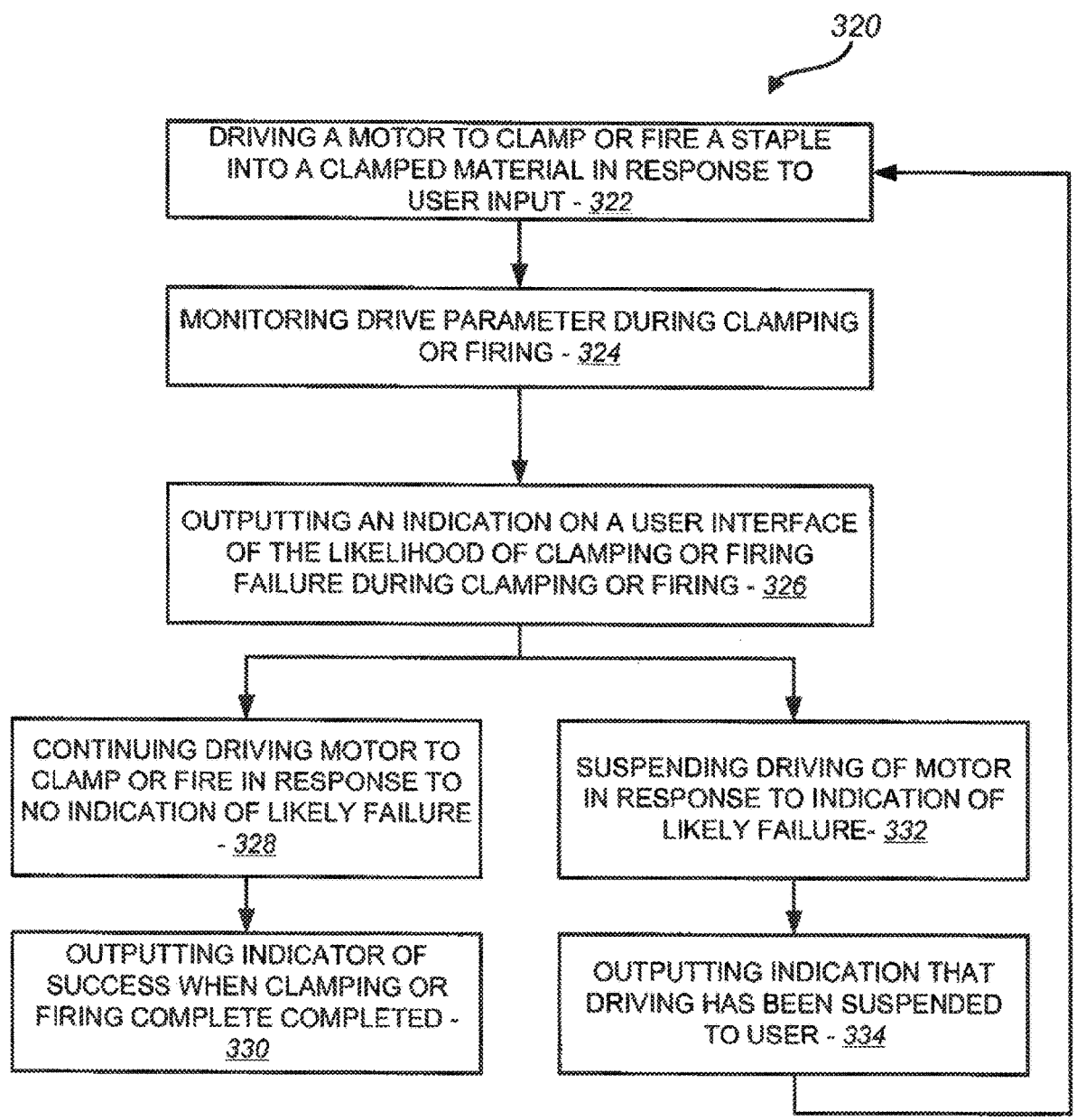

FIGS. 17-19 graphically illustrate embodiments of the claimed methods. FIG. 17 is a simplified representation of exemplary method 300. Method 300 includes a step 302 of monitoring a drive parameter of a motor driving a tool to clamp and a step 304 of outputting an indication on a user interface of a likelihood of clamping failure during clamping in response to the monitored drive parameter. FIG. 18 is a simplified representation of exemplary method 304. Method 304 includes a step 305 of monitoring a drive parameter of a motor driving a tool to fire a staple into a clamped material and a step 307 of outputting an indication on a user interface of a likelihood of firing failure during firing in response to the monitored drive parameter. FIG. 19 is a simplified representation of a method 310 which further includes the step 312 of driving a motor to clamp a tissue in response to a user input to clamp, a step 314 of monitoring a drive parameter of the motor during clamping of the tissue, a step 316 of outputting an indication of a likelihood of clamping failure during clamping in response to the monitored drive parameter, and a step 318 of suspending driving of the motor if there is an indication of likely failure or continuing driving of the motor if there is no indication of likely failure. FIG. 20 is a simplified representation of a method 320 which includes step 322 of driving a motor to clamp or fire a staple into a clamped material in response to a user input, step 324 of monitoring a drive parameter during clamping or firing, step 326 of outputting an indication on a user interface of the likelihood of clamping or firing failure during clamping or firing. If there is no indication of likely failure, then the method of 320 further includes step 328 of continuing driving the motor to clamp or fire and step 330 of outputting a message of success when clamping or firing complete. If there is an indication of likely failure, then the method of 320 further includes step 332 of suspending driving of the motor in response to the indication and step 334 of outputting an indication that the driving parameter has been suspended.

Figure 21:
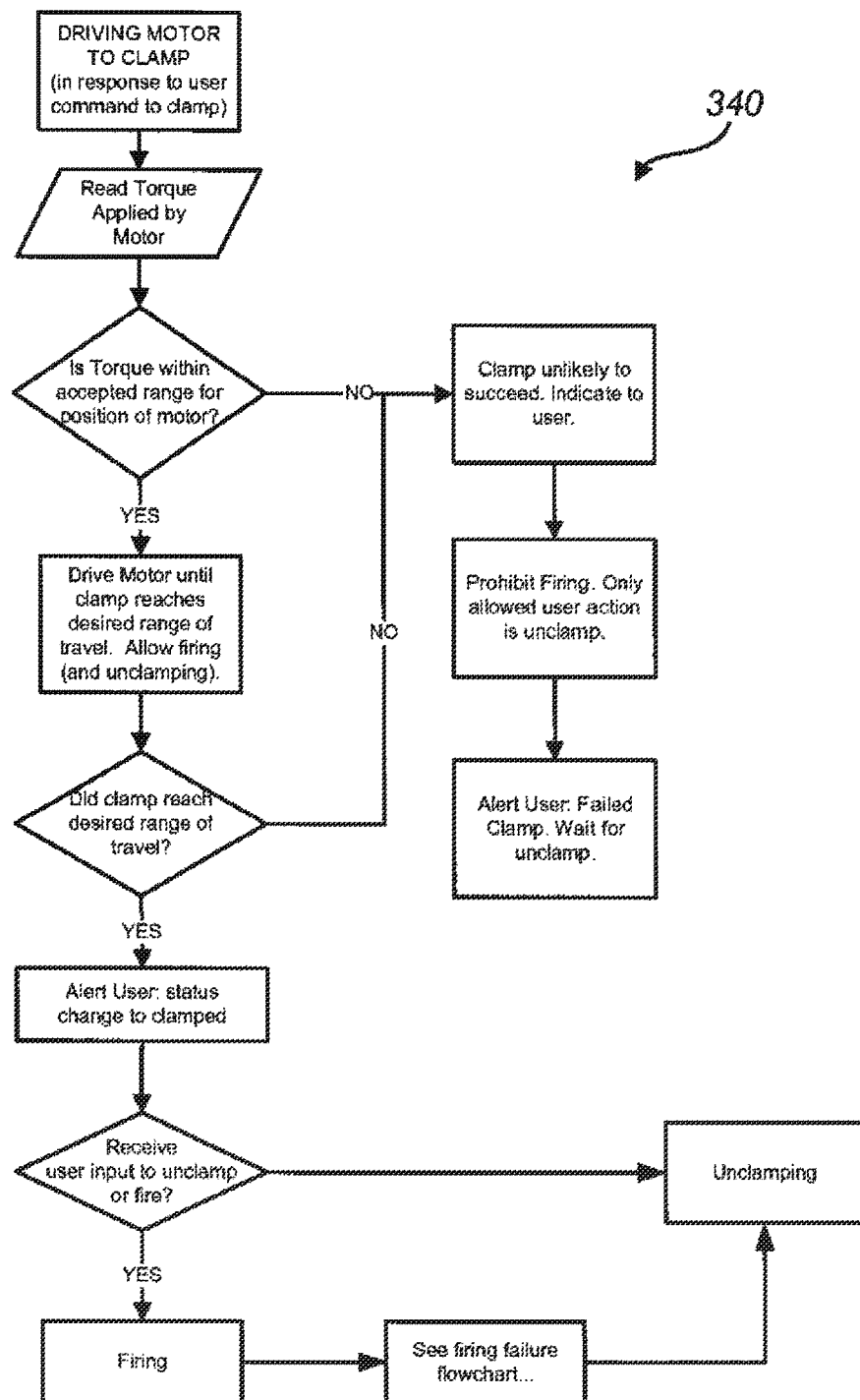
FIGS. 21-22 illustrate flow charts utilizing methods in accordance with many embodiments.
Figure 22:
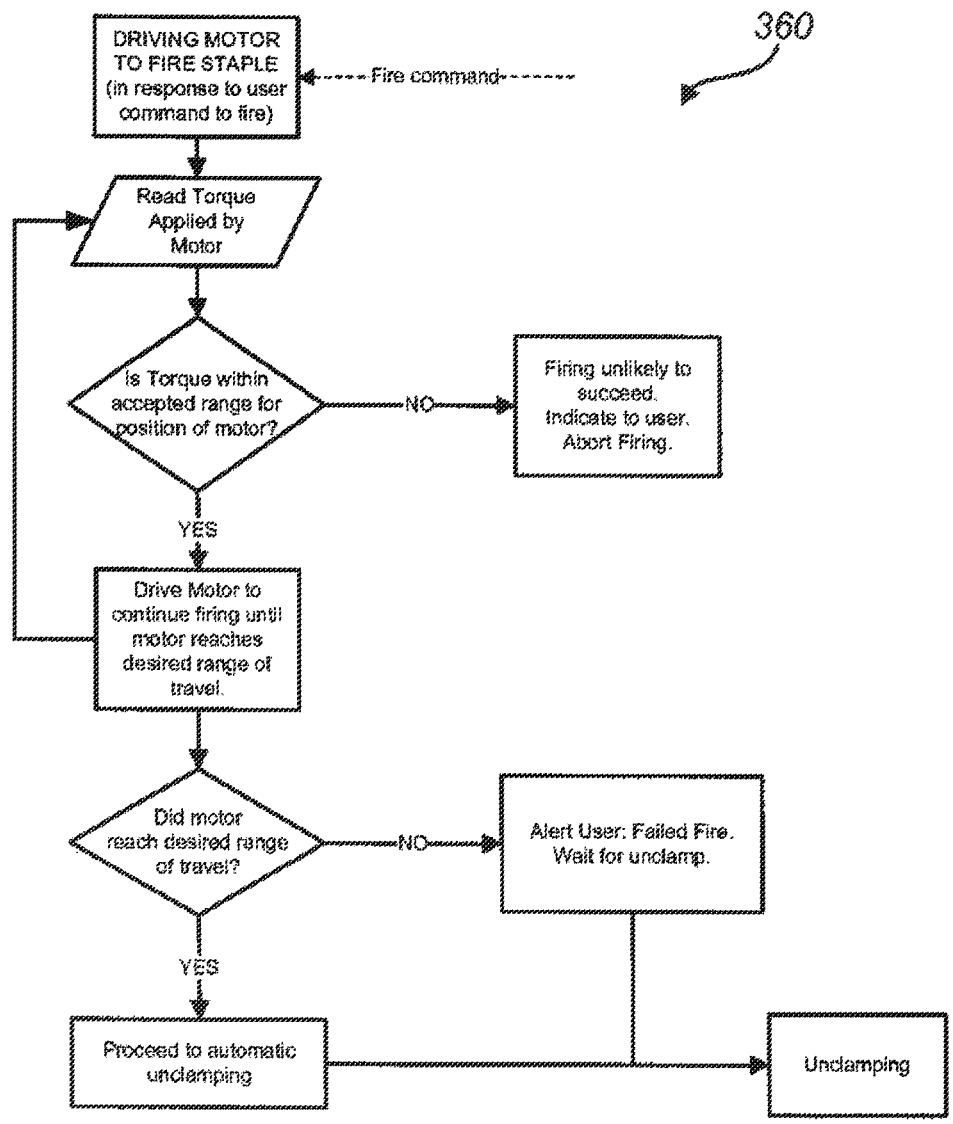

FIGS. 21-22 depict flowcharts illustrating embodiments of the claimed methods. FIG. 21 is a flow chart showing an embodiment of the claimed method as applied to clamping as it would be incorporated into a minimally invasive robotic surgical system. FIG. 22 is a flow chart showing an embodiment of the claimed method as applied to firing of a staple into clamped tissue as it would be incorporated into the robotic surgical system of FIG. 20. The described robotic system may require user input to command the system to clamp and/or firing the staple into the clamped tissue.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well.

Other embodiments in accordance with the present disclosure will be apparent to those skilled in the art from consideration of the specification and practice of the teachings disclosed herein. It is intended that the specification and examples be considered as exemplary only, with a true scope and spirit being indicated by the following claims.

What is claimed is:

1. A system, comprising:
    a surgical instrument comprising:
        an end effector comprising a first jaw member and a second jaw member, the second jaw member comprising or being configured to receive a plurality of staples, and
        an actuation mechanism operably coupled to the end effector to actuate the end effector to perform at least one of a clamping procedure or a staple firing procedure;
    a drive system configured to drive the actuation mechanism;
    a controller operably coupled to the drive system; and
    a user interface operably coupled to the controller,
    wherein the controller is configured to:
        determine the clamping procedure or the staple firing procedure has failed based on a magnitude of an actuation force applied by the drive system to the actuation mechanism; and
        cause the user interface to output a failure indication indicative of the failure.

2. The system of claim 1, wherein the actuation mechanism is operably coupled to the end effector to actuate the end effector to perform the clamping procedure, the clamping procedure comprising closing the first and second jaw members to clamp material between the first and second jaw members.

3. The system of claim 2, wherein a failure of the clamping procedure comprises at least one of:
    the actuation mechanism being jammed;
    the material being absent between the first and second jaw members during closing of the first and second jaw members; or
    the material being resistant to clamping.

4. The system of claim 1, wherein the actuation mechanism is operably coupled to the end effector to actuate the end effector to perform the staple firing procedure, the staple firing procedure comprising applying one or more of the plurality of staples to staple material clamped between the first and second jaw members.

5. The system of claim 4, wherein a failure of the staple firing procedure comprises at least one of:
    the actuation mechanism being jammed;
    one or more of the plurality of staples being absent from the second jaw member; or
    the material being resistant to stapling.

6. The system of claim 1, wherein the controller is further configured to:
    compare the magnitude of the actuation force to a threshold; and
    determine that the clamping procedure or the staple firing procedure has failed in response to the magnitude of the actuation force being less than the threshold.

7. The system of claim 1, wherein the controller is configured to:
    compare the magnitude of the actuation force to a threshold; and
    determine that the clamping procedure or the staple firing procedure has failed in response to the magnitude of the actuation force being greater than the threshold.

8. The system of claim 1, wherein the controller is configured to:
    compare the magnitude of the actuation force to a first threshold and to a second threshold; and
    determine that the clamping procedure or the staple firing procedure has failed in response to at least one of:
        the magnitude of the actuation force being less than the first threshold; or
        the magnitude of the actuation force being greater than the second threshold.

9. The system of claim 1, wherein the controller is further configured to:
    determine the magnitude the actuation force at a plurality of timings during performance of the clamping procedure or the staple firing procedure;
    compare the magnitude of the actuation force at each of the plurality of timings to a threshold; and
    determine that the clamping procedure or the staple firing procedure has failed in response to the magnitude of the actuation force at any one of the plurality of timings satisfying the threshold.

10. The system of claim 9, wherein:
    a value of the threshold varies during performance of the clamping procedure or staple firing procedure.

11. The system of claim 10, wherein:
    the value of the threshold varies during performance of the clamping procedure or staple firing procedure based on an amount of displacement of the drive system or actuation mechanism.

12. The system of claim 11, further comprising:
    one or more sensors operably coupled to the controller and configured to sense at least one of: the magnitude of the actuation force, the amount of displacement of the drive system, or the amount of displacement of the actuation mechanism.

13. The system of claim 1, wherein:
    the drive system comprises a motor; and
    the actuation force comprises a torque generated by the motor.

14. A system, comprising:

a surgical instrument comprising:

an end effector comprising a first jaw member and a second jaw member, the second jaw member comprising or being configured to receive a plurality of staples, and an actuation mechanism operably coupled to the end effector to actuate the end effector to perform at least one of a clamping procedure or a staple firing procedure;

a drive system configured to drive the actuation mechanism;

a controller operably coupled to the drive system; and a user interface operably coupled to the controller, wherein the controller is configured to:

compare a magnitude of an actuation force applied by the drive system to the actuation mechanism to a threshold; and cause the user interface to output a failure indication in response to the magnitude of the actuation force being less than the threshold.

15. The system of claim 14, wherein:

a value of the threshold varies during performance of the clamping procedure or staple firing procedure; and the controller is further configured to:

determine the magnitude of the actuation force at a plurality of timings during performance of the clamping procedure or the staple firing procedure;

compare the magnitude of the actuation force measured at each of the plurality of timings to the threshold; and determine that the clamping procedure or the staple firing procedure has failed in response to the magnitude of the actuation force at any timing of the plurality of timings being less than the value of the threshold at the respective timing.

16. The system of claim 15, wherein:

the value of the threshold varies during performance of the clamping procedure or staple firing procedure based on an amount of displacement of the drive system or actuation mechanism.

17. The system of claim 14, wherein:

the drive system comprises a motor; and the actuation force comprises a torque generated by the motor.

18. A system, comprising:

a surgical instrument comprising:

an end effector comprising a first jaw member and a second jaw member, the second jaw member comprising or being configured to receive a plurality of staples, and an actuation mechanism operably coupled to the end effector to actuate the end effector to perform at least one of a clamping procedure or a staple firing procedure;

a drive system configured to drive the actuation mechanism;

a controller operably coupled to the drive system; and a user interface operably coupled to the controller, wherein the controller is configured to:

compare a magnitude of an actuation force applied by the drive system to the actuation mechanism to a threshold; and cause the user interface to output a failure indication in response to the magnitude of the actuation force being greater than the threshold.

19. The system of claim 18, wherein:

a value of the threshold varies during performance of the clamping procedure or staple firing procedure; and the controller is further configured to:

determine the magnitude of the actuation force at a plurality of timings during performance of the clamping procedure or the staple firing procedure;

compare the magnitude of the actuation force measured at each of the plurality of timings to the threshold; and determine that the clamping procedure or the staple firing procedure has failed in response to the magnitude of the actuation force at any timing of the plurality of timings being greater than the value of the threshold at the respective timing.

20. The system of claim 19, wherein:

the value of the threshold varies during performance of the clamping procedure or staple firing procedure based on an amount of displacement of the drive system or actuation mechanism.

\* \* \* \* \*